US007878652B2

(12) United States Patent
Chen et al.

(10) Patent No.: US 7,878,652 B2
(45) Date of Patent: Feb. 1, 2011

(54) ADAPTIVE PHOTOSCREENING SYSTEM

(75) Inventors: Ying-Ling Ann Chen, Tullahoma, TN (US); James W. L. Lewis, Tullahoma, TN (US)

(73) Assignee: University of Tennessee Research Foundation, Knoxville, TN (US)

(*) Notice: Subject to any disclaimer, the term of this patent is extended or adjusted under 35 U.S.C. 154(b) by 66 days.

(21) Appl. No.: 12/234,947

(22) Filed: Sep. 22, 2008

(65) Prior Publication Data

US 2009/0079937 A1    Mar. 26, 2009

Related U.S. Application Data

(63) Continuation-in-part of application No. 11/338,083, filed on Jan. 24, 2006, now Pat. No. 7,427,135.

(51) Int. Cl.
*A61B 3/14* (2006.01)

(52) U.S. Cl. .................. 351/206; 351/205; 351/222; 351/246

(58) Field of Classification Search ................ 351/200, 351/205, 206, 210, 222, 246, 221
See application file for complete search history.

(56) References Cited

U.S. PATENT DOCUMENTS

| | | | |
|---|---|---|---|
| 4,989,968 A | 2/1991 | Freedman | |
| 5,249,003 A | 9/1993 | Kohayakawa | |
| 5,355,895 A | 10/1994 | Hay | |
| 5,502,520 A | 3/1996 | Cibis et al. | |
| 5,632,282 A | 5/1997 | Hay et al. | |
| 5,694,199 A | 12/1997 | Rodriguez | |
| 5,989,194 A | 11/1999 | Davenport et al. | |
| 6,089,715 A * | 7/2000 | Hoover et al. | ............... 351/221 |
| 6,095,989 A | 8/2000 | Hay et al. | |
| 6,523,954 B1 | 2/2003 | Kennedy et al. | |
| 6,808,267 B2 | 10/2004 | O'Neil et al. | |
| 7,247,135 B2 | 7/2007 | Iriyama | |

* cited by examiner

*Primary Examiner*—Huy K Mai
(74) *Attorney, Agent, or Firm*—Thomas, Kayden, Horstemeyer & Risley, LLP; Todd Deveau

(57) ABSTRACT

Briefly described, one embodiment of the system, among others, can be implemented as follows. The system includes a computer control system and an environmental light source that is controlled by the computer control system such that an amount of light provided by the environmental light source is adjusted by the computer control so that ocular parameters of an examinee are within a targeted range. Further, the system includes an irradiation system that provides multiple angle and axial eccentricity illuminations and selective wavelength irradiation based upon instructions received from the computer control system, wherein the computer control system instructs the irradiation system to provide different irradiation characteristics for different screening procedures. Also, the system includes an image detection system that captures ocular images of the examinee, wherein the computer control system analyzes captured images and provides results of in-situ analysis. Other systems and methods are also provided.

22 Claims, 22 Drawing Sheets

| TEST FUNCTION | ENVIRONMENT/VIDEO LIGHT CONDITION | RADIATION SOURCE |
|---|---|---|
| 310 BINOCULAR REFRACTION MEASUREMENT | BRIGHT RED-FREE RADIATION ADAPT TO PUPIL RESPONSE TO LIGHT | PULSED NIR RADIATION INTENSITY ADAPTS TO EXAMINEE RETINAL REFLECTANCE |
| 320 FIXATION & ALIGNMENT MEASUREMENT | BRIGHT BLUE-FREE ROOM LIGHT | CONTINUOUS BLUE LIGHT |
| 330 OPTICAL OPACITY & CORNEA MEASUREMENT | DARK ROOM | PULSED NIR |
| 340 RETINA SPECTRUM MEASUREMENT | DARK ROOM | PULSE WHITE (BROAD BAND SPECTRUM) |
| 350 COLOR BLINDNESS TEST | ARBITRARY | NO RADIATION SOURCE |

FIGURE 4

| AGE | SUGGESTION OF EXAMS BY MD | APS AGE-SPECIFIC PROCEDURE |
|---|---|---|
| NEW BORN ~ 6 MONTHS | CORNEA LIGHT REFLEX | 330 OPTICAL OPACITY & CORNEA MEASUREMENT |
| | RED REFLEXES | 340 RETINA SPECTRUM MEASUREMENT |
| 6 MONTHS ~ 3 1/2 YEARS | FIXATION TO LIGHT OR SMALL TOYS, MONOCULAR OCCLUSION, CORNEAL LIGHT REFLEX TEST, COVER/UNCOVER TEST, RED REFLEX | 320 BINOCULAR FIXATION & ALIGNMENT MEASUREMENT |
| | | 330 OPTICAL OPACITY & CORNEA MEASUREMENT |
| | | 340 RETINA SPECTRUM MEASUREMENT |
| 3 1/2 YEARS ~ 5 YEARS | VISUAL ACUITY | 310 BINOCULAR REFRACTION MEASUREMENT |
| | CORNEAL LIGHT REFLEX TEST | 320 BINOCULAR FIXATION & ALIGNMENT MEASUREMENT |
| | COVER/UNCOVER TEST | 330 OPTICAL OPACITY & CORNEA MEASUREMENT |
| | FUNDUS EXAM | 340 RETINA SPECTRUM MEASUREMENT |
| | COLOR BLINDNESS TEST (NURSE) | 350 COLOR BLINDNESS TEST |
| 5 YEARS ~ 12 YEARS | VISUAL ACUITY | 310 BINOCULAR REFRACTION MEASUREMENT |
| | CORNEAL LIGHT REFLEX TEST | 320 BINOCULAR FIXATION & ALIGNMENT MEASUREMENT |
| | COVER/UNCOVER TEST | 330 OPTICAL OPACITY & CORNEA MEASUREMENT |
| | FUNDUS EXAM | 340 RETINA SPECTRUM MEASUREMENT |
| | COLOR BLINDNESS TEST (NURSE) | 350 COLOR BLINDNESS TEST |
| 12 YEARS OR OLDER | SAME AS ABOVE | 310 BINOCULAR REFRACTION MEASUREMENT |
| | | 330 OPTICAL OPACITY & CORNEA MEASUREMENT |
| | | 340 RETINA SPECTRUM MEASUREMENT |

- START DATA ACQUISITION TO OBTAIN PATIENT INFORMATION AND OBTAIN OCULAR IMAGES 910
- PERFORM IMAGE ANALYSIS ON ACQUIRED IMAGES 920
- VERIFY ACQUIRED DATA IS SUFFICIENT FOR SUBSEQUENT ANALYSIS 930
- OBTAIN NEW DATA, IF NECESSARY 940
- ANALYZE IMAGE DATA FOR ABNORMALITIES 950
- IF NEGATIVE RESULTS, REPORT RESULTS TO EXAMINEE 960
- IF POSITIVE RESULTS, REPORT RESULTS AND PROVIDE REFERRAL 970

FIGURE 12
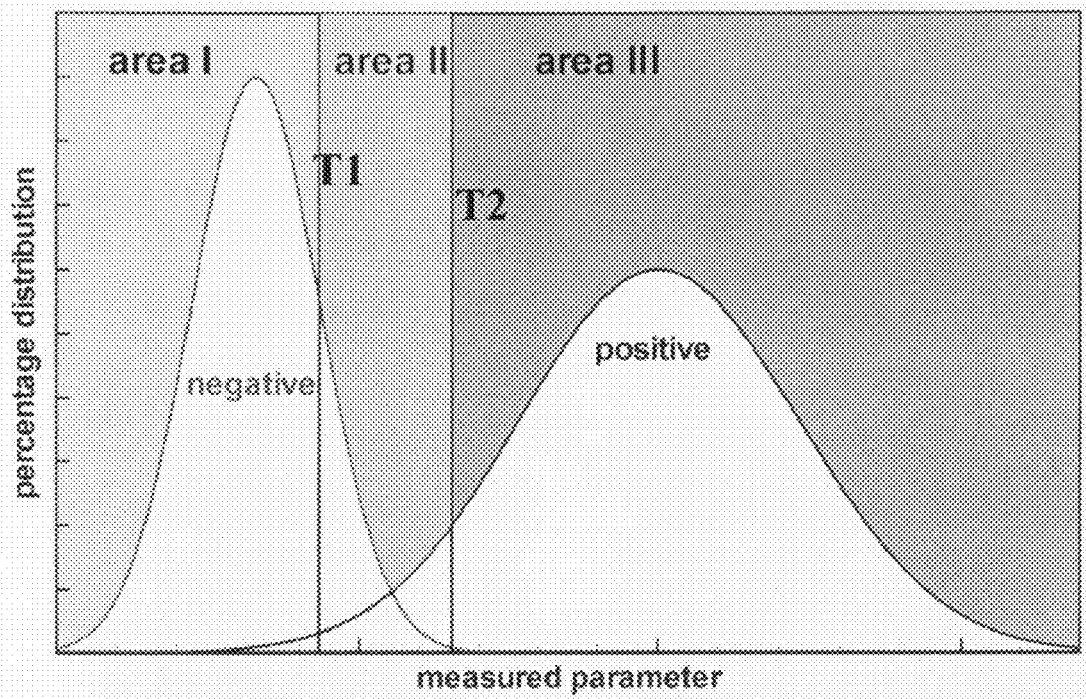
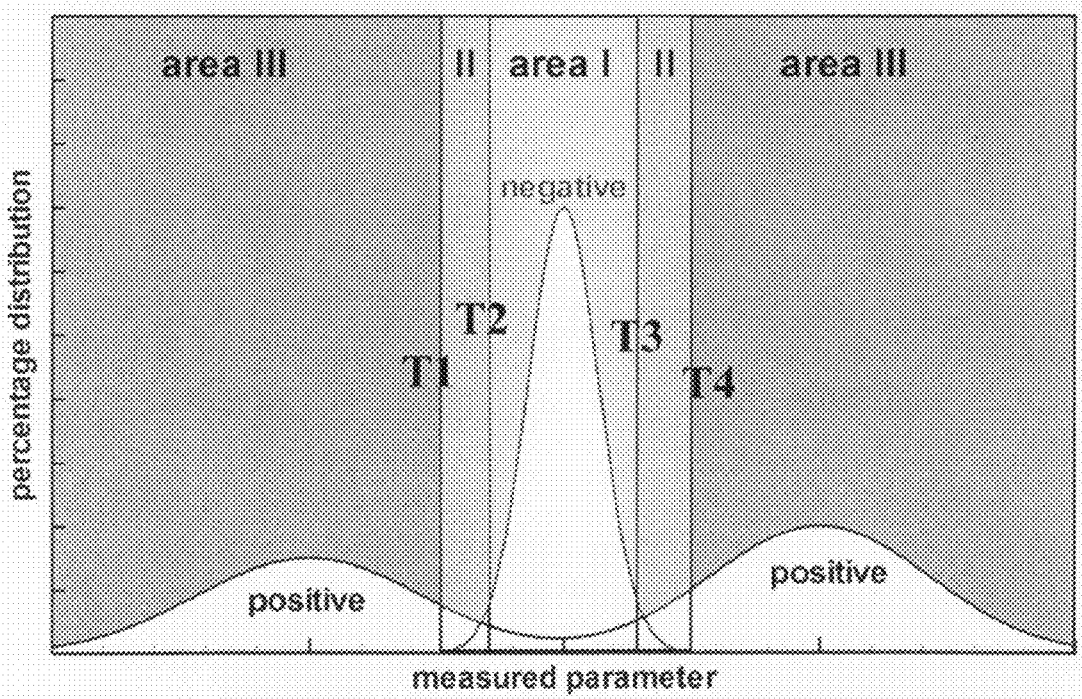
FIGURE 13

ADAPTIVE PHOTOSCREENING SYSTEM

CROSS-REFERENCE TO RELATED APPLICATION

This application is a continuation-in-part of U.S. utility application entitled, "Adaptive Photoscreening System," having Ser. No. 11/338,083, filed Jan. 24, 2006, now U.S. Pat. No. 7,427,135 which is entirely incorporated herein by reference

TECHNICAL FIELD

The present disclosure is generally related to medical screenings and, more particularly, is related to ocular screening and analysis techniques.

BACKGROUND

Vision disorders affect over 150 million Americans and are the most prevalent handicapping conditions in childhood. Early detection of vision disorder increases the likelihood of effective treatment that can decrease the negative impact of vision disorders and can improve the quality of life.

Vision screening is particularly important at early age. The American Academy of Pediatrics (AAP), American Academy of Opthalmology (AAO), American Association for Pediatric Opthalmology and Strabismus (AAPOS), and American Optometric Association (AOA) recommend that vision screening should be performed at the earliest possible age and at regular intervals during childhood. However, more than 85% of preschool children have never received comprehensive eye examinations, and more than 78% of preschool children have never received any type of vision screening. Further, a 1999 report of American Foundation for Visual Awareness indicates that school vision screening identifies only one out of four children who have vision problems.

Some vision problems, if undetected and untreated, can prevent proper development of the brain's binocular function, such as a condition of amblyopia or lazy eye. Because children's eyesight and ocular functions are not fully developed until age 5-6, the damage can be permanent unless the "neglected" eye is corrected before the critical age of 5-6. The most common causes of amblyopia (2-5% in the US) are anisometropia (the refractive error difference between two eyes) and strabismus (crossed eyes, 3-4% in the U.S.). However, no current device that is appropriate for large-scale screening simultaneously satisfies multi-functional assessment requirements of AAP guidelines with the desired performance of efficiency and accuracy, or sensitivity and specificity.

Thus, a heretofore unaddressed need exists in the industry to address the aforementioned deficiencies and inadequacies.

SUMMARY

Embodiments of the present disclosure provide systems and methods for performing customized photoscreening. Briefly described, one embodiment of the system, among others, can be implemented as follows. The system includes a computer control system and an environmental light source that is controlled by the computer control system such that an amount of light provided by the environmental light source is adjusted by the computer control so that ocular parameters of an examinee are within a targeted range. Further, the system includes an irradiation system that provides multiple angle and eccentricity illuminations and selective wavelength irradiation based upon instructions received from the computer control system, wherein the computer control system instructs the irradiation system to provide different irradiation characteristics for different screening procedures. Also, the system includes an image detection system that captures ocular images of the examinee, wherein the computer control system analyzes captured images and provides results of in-situ analysis. In an additional embodiment, the computer control system displays a video feature to the examinee, where ocular movement and accommodation of the examinee is controlled by use of the video feature.

Embodiments of the present disclosure can also be viewed as providing methods for performing ocular photoscreening. In this regard, one embodiment of such a method, among others, can be broadly summarized by the following steps: performing an automated screening procedure; analyzing the ocular images to assess at least one ocular condition; and providing results from the analyzing step, where the screening procedure includes the steps of: adjusting environmental lighting so that ocular parameters of an examinee are within a targeted range; displaying a video feature to direct focus of an examinee in a desired location; and acquiring ocular images of the examinee.

Other systems, methods, features, and advantages of the present disclosure will be or become apparent to one with skill in the art upon examination of the following drawings and detailed description. It is intended that all such additional systems, methods, features, and advantages be included within this description and be within the scope of the present disclosure.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 4 is a table showing adaptive illumination controls for a variety of test functions of one embodiment of the APS system of FIG. 1.

FIG. 5 is a table displaying age- and gender-specific procedures that are performed in one embodiment of the APS system of FIG. 1.

FIG. 9 is a flow chart describing one embodiment of an auto-analysis procedure for one embodiment of the APS system of the FIG. 1.

FIGS. 12-13 are diagrams of a two-outcome frequency distribution function for a measured parameter by one embodiment of the APS system of FIG. 1.

DETAILED DESCRIPTION

Early detection of abnormal conditions or vision problems is desirable and is very important, because such conditions are threatening to life, sight, and/or development. This need exists in the U.S. and even more so in developing nations and other nations where medical resources are severely limited. Accordingly, one embodiment, among others, of the present disclosure provides in situ, real-time computer analysis of ocular images to determine and classify photoscreening image results as normal or abnormal in each of five screening areas. Further, in accordance with the present disclosure, non-medical personnel may perform screening tests using a comparatively inexpensive ocular screening device, which is characterized by transportability and robustness.

Figure 1:
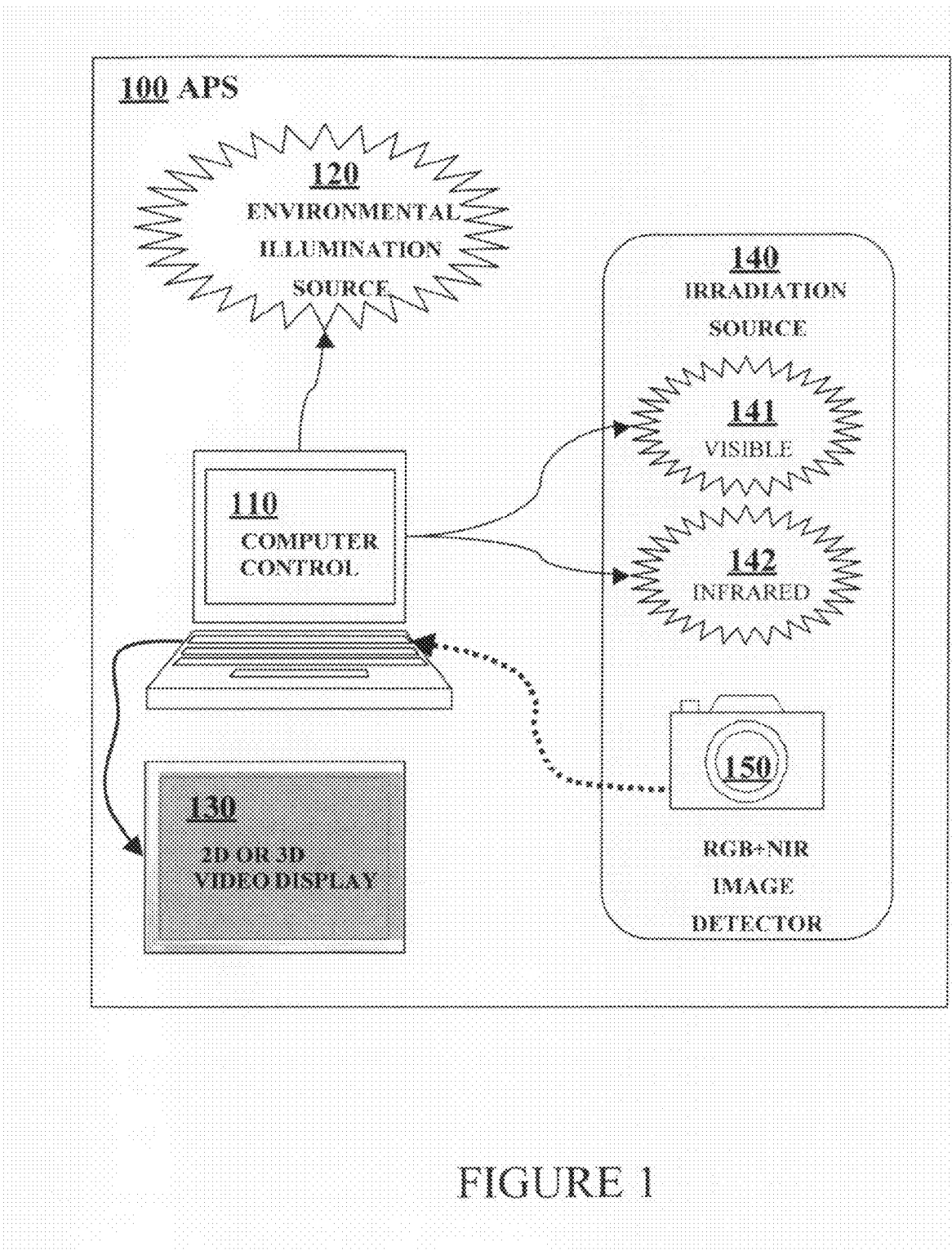
FIG. 1 is a block diagram representing one embodiment of an Adaptive Photoscreening System (APS) of the present disclosure.

FIG. 1 shows one embodiment of an Adaptive Photoscreening System (APS) 100 of the present disclosure. APS 100 applies advanced photoscreening technology along with eye tracking, dynamic visual stimulus, and computer-assisted image interpretation to enhance the accuracy of vision screening as requirement described by AAP guidelines. The evaluation processes of embodiments of APS 100 include ocular analysis & assessments, such as those involving binocular refraction condition, ocular motility & alignment, optical opacities, cornea irregularity, retinal tumors, and color-blindness. Therefore, one embodiment of the APS system 100 is an integrated ocular screening system that incorporates advanced imaging that may assist physicians, nurses, educational institutions, public health departments, and other professionals who perform vision evaluation services. As such, embodiments of the APS system 100 remedy many known deficiencies of current screening devices.

Elements of the APS system 100, in one embodiment, include computer-controlled visible ocular-irradiation source(s) 141, near-infrared (NIR) ocular-irradiation source(s) 142, environmental radiation source 120, visual stimulus video screen 130, visible and infrared digital image detector 150, and computer control 110 for performing registration, monitoring, calibration, testing control, quality control, and auto-analysis algorithms, among other functions. Note, in some embodiments the visible and infrared image detector 150 constitutes individual infrared and visible cameras. While in some embodiments, a single camera may be used to obtain infrared and visible images.

As such, the APS system 100 provides temporal and spatial resolutions that are used to provide ample sensitivity and specificity for detection of ocular function and abnormalities; quantitative assessment of results needed for making medical referral determinations; and provisions for both local data archival and also electronically transmitted remote data archival.

Figure 2:
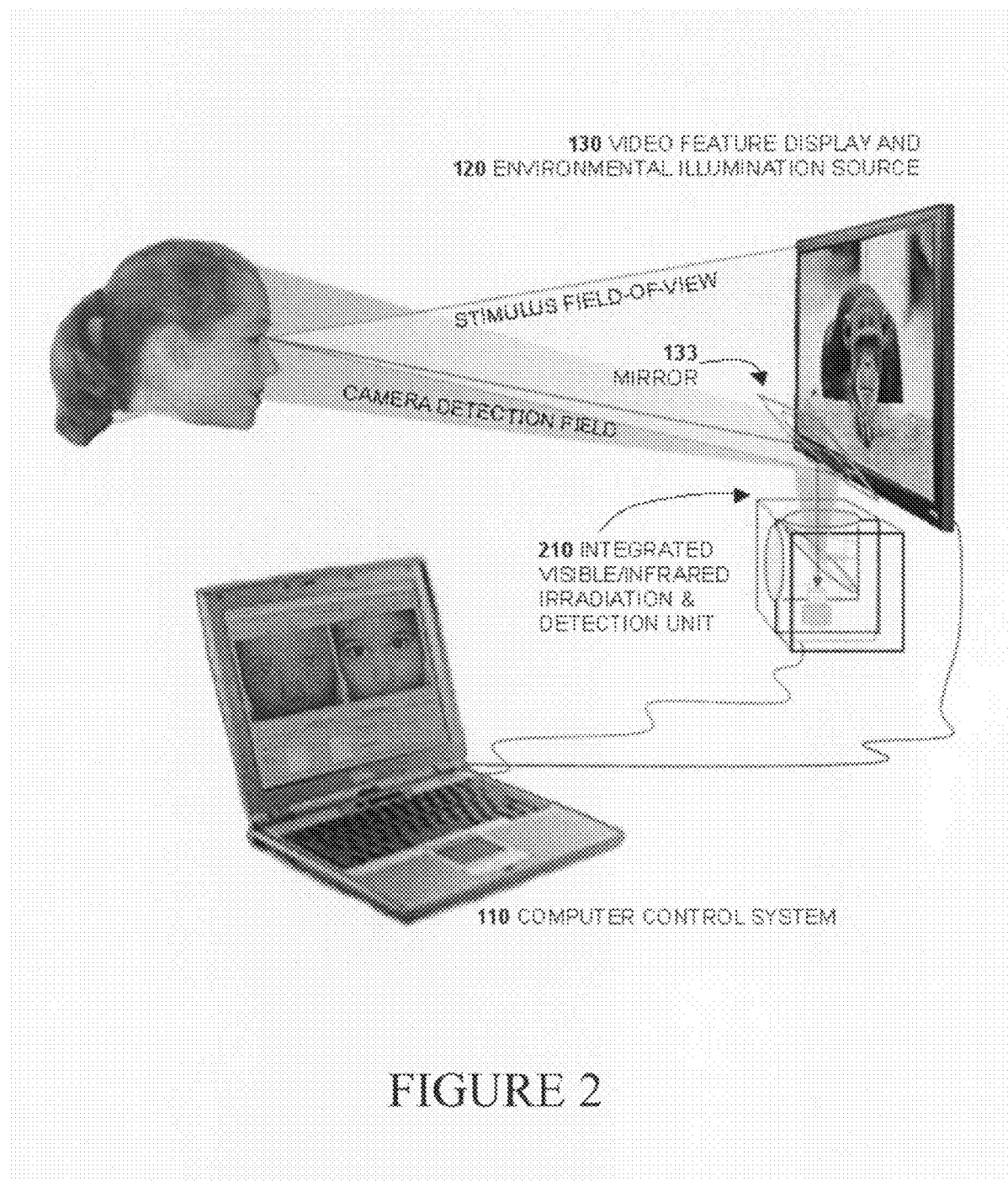
FIG. 2 is diagram of a perspective view of a layout of the APS system of FIG. 1.

In one embodiment, the near-infrared ocular irradiation source 142 includes a two-dimensional infrared display (e.g., infrared LED assembly), and the visible ocular irradiation source 141 includes a visible light source display, which may be constructed with visible LEDs in selected wavelengths. A digital image detector 150 includes a multi-frame digital camera that is capable in detecting both visible (RGB) and infrared signals, an optical beam splitter, and a mirror. In one embodiment, the near-infrared ocular irradiation source 142, the visible ocular irradiation source 141, and the digital image detectors 150 are assembled and fixed at a lower section of the video screen 130, which may be a LCD flat screen, as shown in FIG. 2. This portion of the APS 100 is lightweight and is easy to position directly in front of an examinee.

Also shown in FIG. 2, in one embodiment, an adjustable mirror 133 may be positioned between the integrated camera/irradiation source unit 210 and the video feature display 130, to align the stimulus field-of-view of the examined eye and the detection field of the camera. For an infrared application, mirror 133 may be a hot mirror that reflects near 100% of infrared. For visible application, mirror 133 may be a mirror or optical beam splitter. When beam splitter is used, the portion of video display behind the beam splitter acts as the visible irradiation source.

The environmental illumination source 120 may be the illumination produced by the programmed video 130 itself or, when the illumination is not sufficient in control of pupil response, some visible LEDs posited by the sides of the video display 130.

Figure 3:
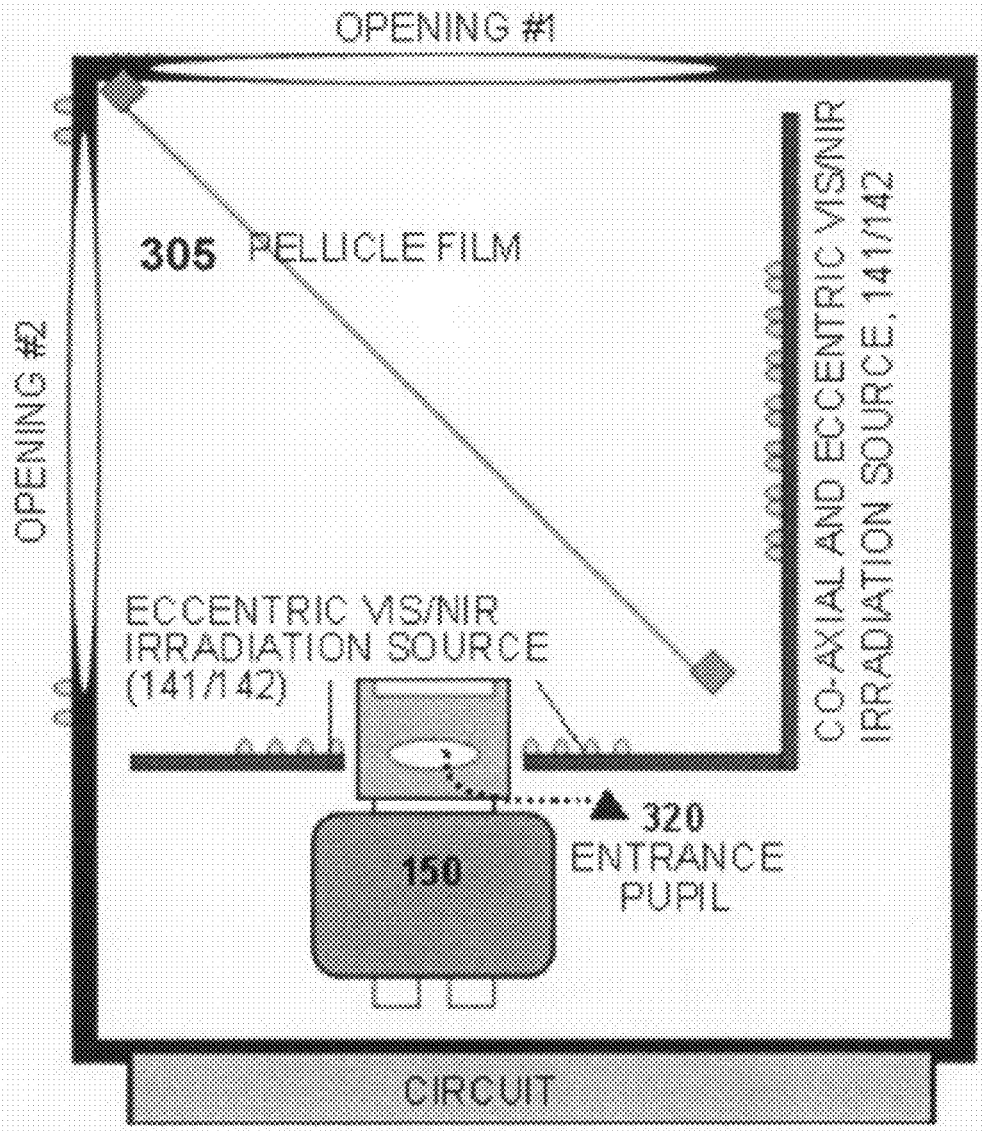
FIG. 3 is a diagram of a setup that may be used for either the infrared or visible camera systems of FIG. 1, for one embodiment.

FIG. 3 shows a possible arrangement of the integrated camera/irradiation source unit 210. The coaxial irradiation is produced by the use of a pellicle beam splitter 305. The coaxial light source may be one of the LEDs on the right panel that is projected onto the center of the entrance pupil 320 of the detector 150. If the size of LED is small compared to the camera pupil size, multiple irradiation sources (LEDs) become near-coaxial. Eccentric irradiation is provided by the LEDs arranged on both the right and bottom panels as shown in the figure.

The computer control 110 (e.g., a laptop PC) controls APS 100, including remote optical and light elements (e.g., image detectors 150, LED displays 141, 142, environmental illumination 120, video display 130, etc.). In one embodiment, the computer control 110 is configured to display a user-interface program that enables a trained operator to launch a video feature for the examinee. In one embodiment, the video feature being displayed on the video screen 130 attracts the attention (e.g., controls accommodation status and ocular fixation) of examinees throughout examination procedures. For a young examinee, an animation character of his/her choice may be used in the screening procedure. Via the video camera 150 and a small continuous irradiation, an operator ensures that the examinee is properly positioned within the field-of-view of one camera. Infrared irradiation can provide strong retinal reflex for the detector that is invisible to examinee. While the examinee is watching the animation, the examinee's cornea reflections, which determine his/her ocular gazing angle and convergence, are calculated with the computer control system 110 in real time. The animation feature may be used to control an examinee's ocular motion as well as emotion. For example, an on-screen character within the animation feature may be programmed to "walk off the screen" if the examinee is not in the proper viewing range. Therefore, ocular movement and accommodation can be well controlled by the APS 100 in performing ocular measurements.

The incident light that is projected onto an examinee's retina is diffusively scattered and passes back through all the ocular elements on the return path. The information the light carries (that is captured in the photoscreening image) is in some ways similar to that provided by a wavefront aberration method that describes individual ocular optical performance. However, the information content of the photoscreening image includes measures of at least one or more of five ocular characteristics that are potentially useful for vision screening, such as:

A. Refractive status of eyes that can be obtained by photorefraction theory under proper control of chromatic and monochromatic aberrations as well as the ocular gazing angle;

B. Ocular orientation and convergence that can be obtained through binocular Purkinje reflections using the Hirschberg method;

C. Optical opacities that can be observed through the uniformity and both spectral and spatial radiance distributions of the red-reflex;

D. Retinal tumor that can produce an abnormal spectral, or color, distribution in the retinal reflex; and E. Irregular cornea surface that distorts the shape and the reflected irradiance distribution of the incident light beam similar to the red-reflex observation through the retinoscope and opthalmoscope.

In doing so, the APS 100 provides environmental illumination control that adapts to an individual's pupillary response to light and radiation source (141, 142) intensity that adjusts to individual retinal reflectance. FIG. 4 is a table showing adaptive illumination controls for a variety of test functions.

As shown for a refractive test (310), the environmental lighting for the room is bright and adapted in response to examinee's pupil response to the light. A pulsed NIR irradiation source is used, where radiation intensity is adapted in response to the examinee's retinal reflectance. For a fixation and ocular alignment test (320), continuous blue light is provided by the radiation sources and bright, blue-free, light is provided by the environmental light source. For combined optical opacity and cornea examinations (330), pulsed near-infrared radiation is provided by the irradiation sources and the environmental light source is not used so that the room is maintained dark and the examinee's pupils are naturally dilated. For a retina spectrum test (340), pulsed white light (having broad band spectrum that is sensitive to all R, G, and B camera detections) is provided by the radiation sources and the environmental lighting is kept dark for the same reason in 330. For a color blindness test (350), no radiation source is provided and it is arbitrary as to the environmental lighting.

Next, examination procedures are described for one embodiment of the APS 100. First, an operator enters patient data that is provided by an examinee, parent of an examinee, or other adult, while the examinee watches an entry video or animation feature at a preset distance of about two-three of a meter from the examinee. The operator initiates the screening procedure by either touch-screen contact or by programmed LCD (liquid crystal display) sequence based on input patient characteristics or demographics, including age and gender. After which, a variety of tests may then be performed. FIG. 5 displays age- and gender-specific procedures that are performed in one embodiment. These procedures are discussed in greater detail hereinafter.

Via the APS system 100, a data acquisition process is executed. The APS system 100 acknowledges the acquired data in selecting screening procedures that are applicable for the age, gender, and race of the examinee. Further, measurements obtained by the APS system 100 may be calibrated with respect to individual factors obtained from the initial data acquisition process. For example, the variation of the spectral reflectance of individuals can have significant effects on the eccentric measurements. This effect, however, may be eliminated or mitigated by normalizing such data for each eye with the total signal of the corresponding coaxial photoscreening image, as performed in one or more photoscreening procedures of the present disclosure.

Photoscreening Procedures and Tests

A. Binocular Refractive Test

One automated ocular screening procedure performed by an embodiment of the APS system 100 is a binocular refractive test (which corresponds to item 310 in the table of FIG. 4). A binocular refractive test is recommended for persons ages 3½ years and up. For younger children, the logic of the APS system 100 is configured to bypass this test and perform other applicable test(s) for the examinee's age range and gender.

To start the procedure, an examinee is positioned in front of the video screen 130 and is monitored by the infrared video camera 150. The coaxial infrared irradiation (142) is used to illuminate the subject. The infrared images of pupils are captured and the pupil diameters are determined in real time with the computer program. The room or environmental lighting 120 and the video irradiance 130 are red-free to prevent interference of the infrared detection. The illumination from both 120 and 130 are automatically adjusted by the APS system 100 to ensure that the pupil sizes of the examinee are in the proper range of 2.5-4.5 mm. Further, in one or more embodiments, the APS system 100 is configured to play the video (animation) with near constant irradiance before and through the data acquisition. An image detector/irradiation-source unit 210 locates right below a LCD screen 130 and an animation feature being shown on the LCD screen 130 to prevent an eye lash from blocking the reflex signal detected from an eye of the examinee.

A pellicle film beam splitter 305 (as shown in FIG. 3) is used to project the light source space onto a respective camera entrance pupil plane 320 of camera 150 (to provide maximum freedom of light pattern arrangement including all eccentric and coaxial acquisition). This unique technique eliminates the spatial limitation inherent in conventional photoscreening devices. From the viewpoint of the examinee, a respective irradiation source and camera are arranged as shown in FIG.

6A. Also, in some embodiments, small LEDs are used so that cornea reflections are minimized. Fiber optics may be use to provide improved spatial control and beam orientation. Trial lenses (e.g. +1.5 diopter) that compensate the animation display distance (e.g. ⅔ meter) may also be used in front of the subject to relax accommodation for cooperative examinees similar to retinoscopy.

Further, the irradiance of a continuous or pulsed coaxial LED controlled by logic of the APS system 100 may be modulated until the pupil irradiance detected by the infrared camera is just below the detection saturation level. The radiation level of the coaxial LED is then applied to all infrared LEDs before image data acquisition starts.

Figure 6A:
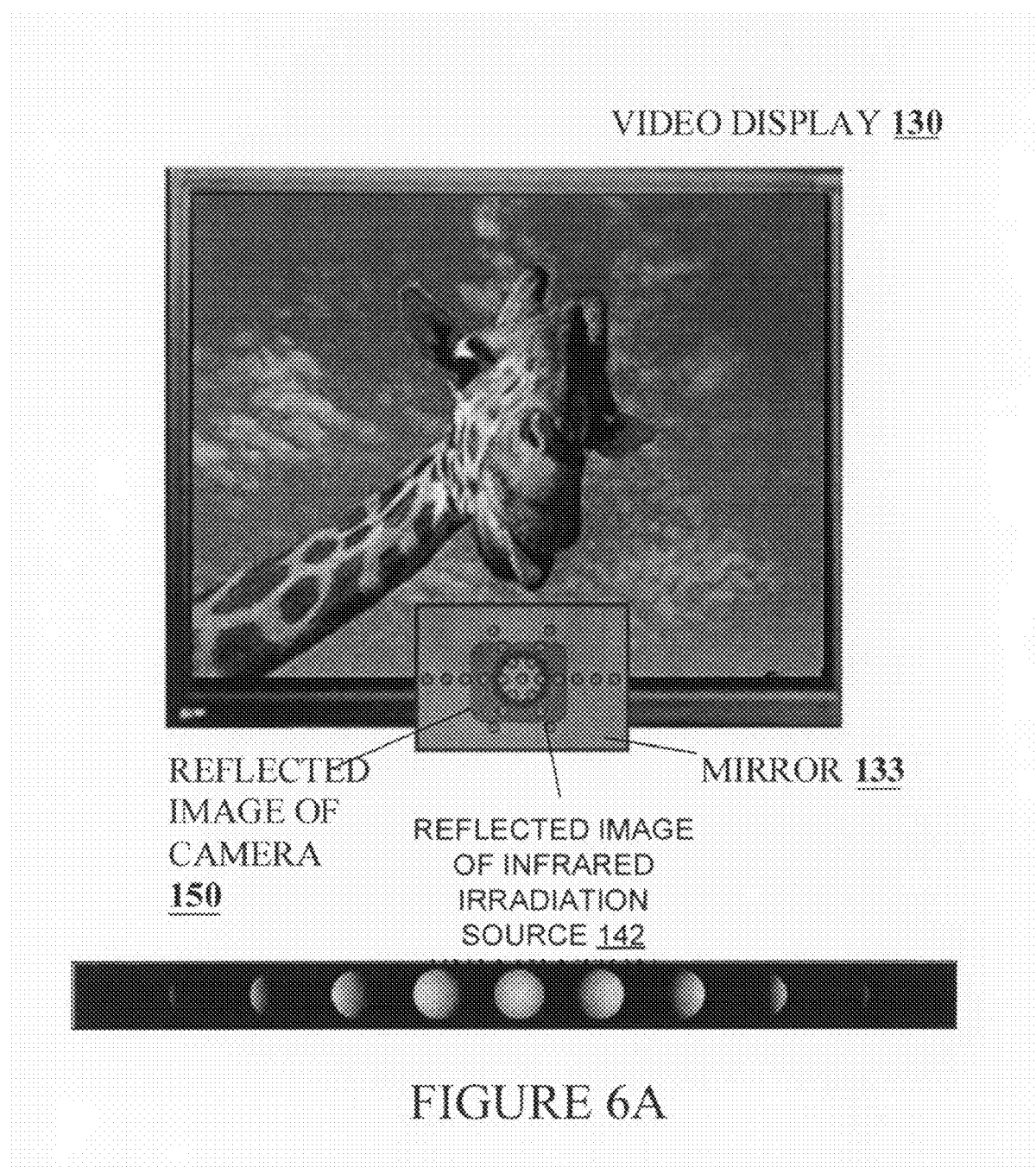
FIG. 6A is a diagram of a setup of an infrared image detection system and irradiation source for a refraction test for one embodiment of the APS system of FIG. 1.

Example photoscreening images of horizontal illumination from an examinee having a +5 diopter measurement are shown in the lower part of the FIG. 6A. The crescent appearances of pupillary images depend not only on the refraction of the eye, but also the pupil size, the gazing angle, and the monochromatic aberration of the eye. The retinal reflex signal from the infrared photoscreening image is used to calibrate retinal properties of an individual. The video digital camera 150 monitors the pupil size to control the aberration and proper subject position and gaze angle of the examinee. The infrared images are acquired and displayed on-screen of the control computer for an operator to see.

Exemplary, the binocular refractive test is initiated by displaying animation characters on a video screen 130, which is used to induce proper positioning of the examinee (e.g., an energetic child). For example, the video screen 130 may display animation feature at a ⅔ meter distance from subject (to provide fixed fixation target at ⅔ m). Ocular images are then taken at 30-60 Hz (for a duration of less than a second) with the sequential programmed activation of irradiation source 142, where a narrow-band wavelength at near infrared is used (instead of white light). This provides multi-eccentric plus coaxial photorefractive data. In particular, an arrangement of a minimum of seven to the maximum of thirty-five LEDs is used in one embodiment as the irradiation source 142.

As the examinee is positioned in front of the video screen 130, logic of the APS system 100 is configured to automatically find two infrared pupil reflections within acquired photoscreening image(s) featuring both eyes and determines the diameters of pupil reflections. If the pupil diameters are larger than 4.5 mm (or smaller than 2.5 mm), the APS system 100 sends a signal to increase (or decrease) the room illumination 120 until the pupil is within 2.5-4.5 mm or reaches its maximum (minimum) illumination. The APS system 100 monitors individually the two pupil reflex irradiances captured by the camera. From the spatially integrated intensity profiles of the sequenced images, refractive errors are determined.

Note, in contrast, that some current, conventional eccentric photorefractive (EPR) screening devices perform this test in a darkened environment to achieve large pupil diameters, which can be 7 nm or more for children. In previous studies, it has been observed that the high-order aberrations for such pupil diameters have significant individual variation that may result in large errors in the visual acuity measurement.

The APS system 100 determines the refractive errors of both eyes from the irradiance provided by a single line of LEDs (at the same angle). The APS system 100 further determines whether astigmatism may exist from the irradiance provided by three lines of LEDs (that are multi-angled), in one embodiment. For example, one embodiment of the APS system is able to detect spherical/cylindrical refractive errors at less than 0.25 diopter measurement, while the axis measurement error is less than 25 degrees for astigmatism. The APS system 100 is able to detect ocular conditions related to spherical, cylindrical, and axis refractive errors; un-equal pupil size (anisocorea); anisometropia; significant infrared irradiance difference from two eyes, etc. via an auto-analysis process, discussed hereinafter.

Figure 6B:
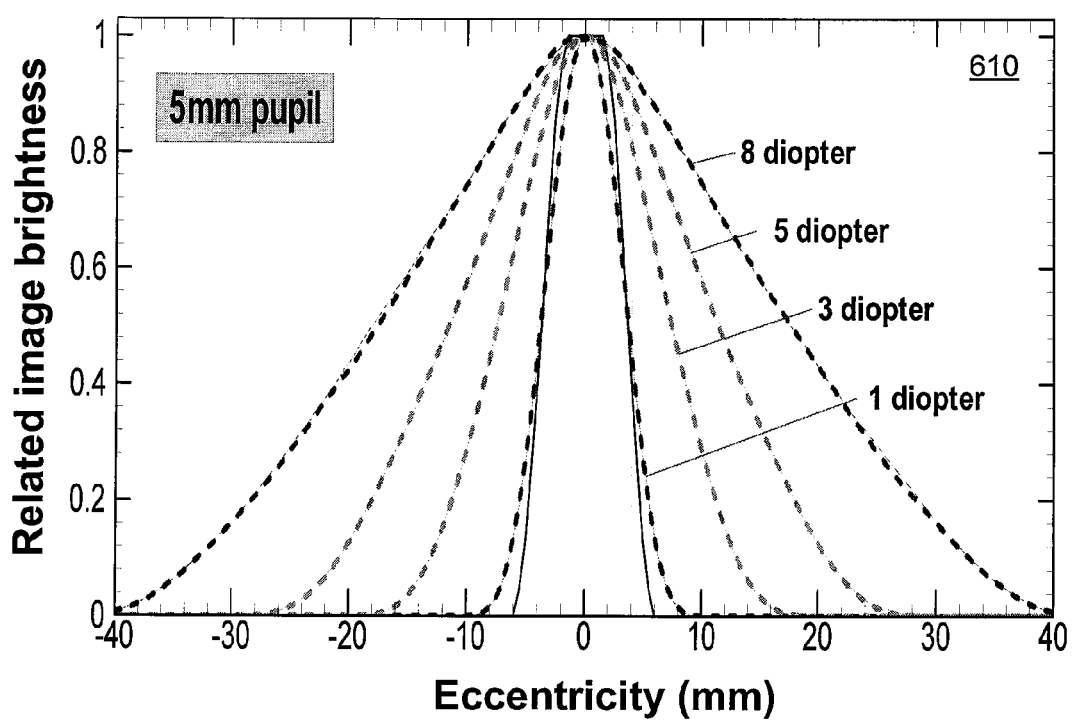
FIG. 6B is a diagram of a bell shape normalized integrated intensity profile used to determine a refractive error by an embodiment of the APS system of FIG. 1.

As described above, one embodiment of the APS system 100 determines the refractive errors of both eyes from the irradiance provided by a single line of LEDs (at the same angle). A bell shape normalized integrated intensity profile 610 (as shown in FIG. 6B) may be obtained by APS 100 and used to determine the refractive error along the meridian of eccentric illumination. In general, it is observed that the intensity bell curve becomes wider with increased pupil diameter and/or refractive error. By calibrating the size of the pupil of the subject to a set size (such as 5 mm), the varying shape of the intensity bell curve may be attributed to a refractive error. For example, in FIG. 6B, the intensity bell curves increase in width as the associated refractive errors increase in dioptive powers.

The term "bell shape", as used above, is meant to relay that the shape of the curve is in a nominal, but known, bell shape—it is not meant to imply that that the curve is strictly speaking a Gaussian-shaped curve.

Figure 6C:
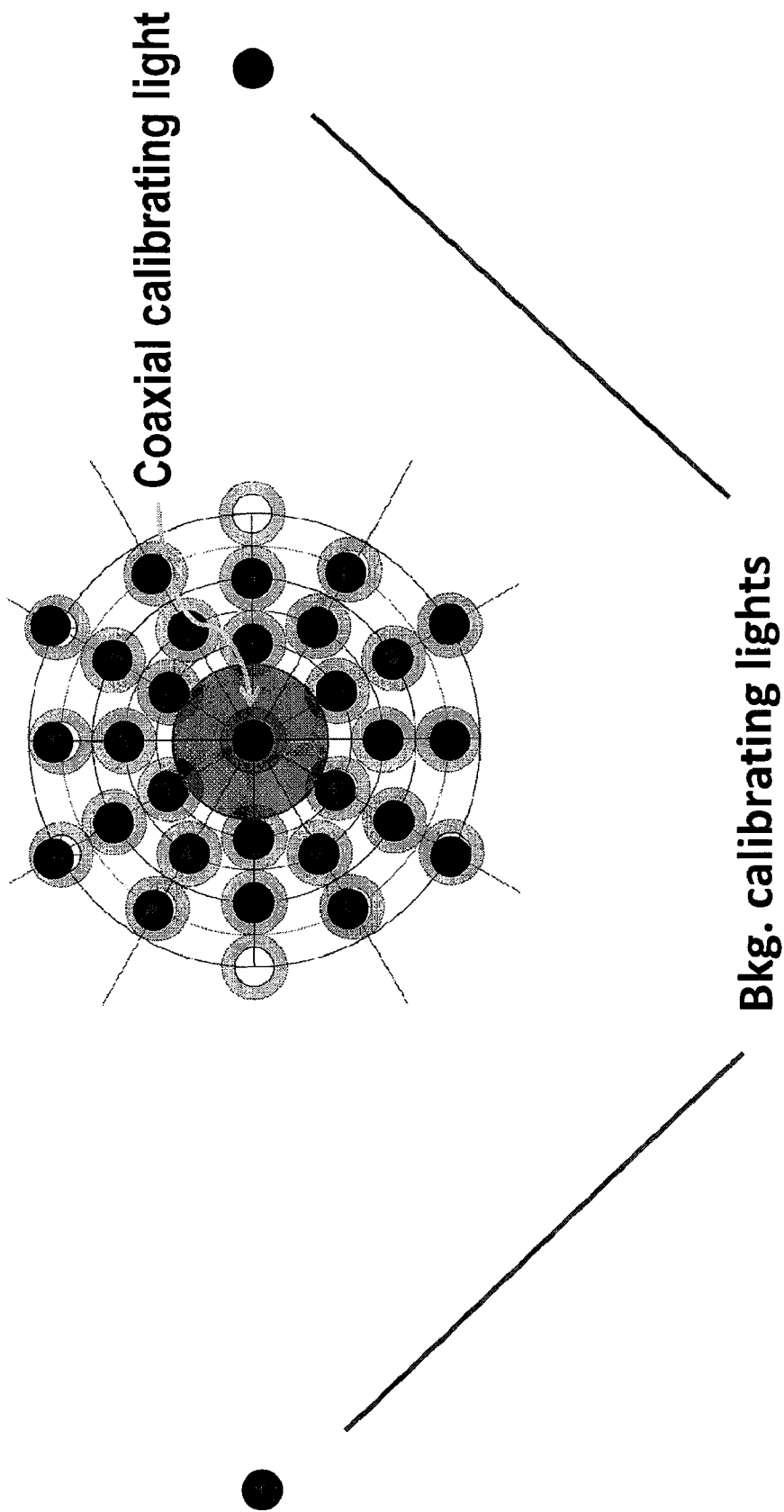
FIG. 6C is a diagram of an irradiance arrangement utilized in an embodiment of the APS system of FIG. 1.

Also, one embodiment of the APS system 100 may utilize irradiance provided by multiple lines of LEDs (at multiple angles) in two dimensions (as shown in FIG. 6C). In FIG. 6C, six lines of LEDs are arranged in a two dimensional pattern. In one embodiment, the inner ring of LEDs extends 15.2 mm from the center with the next set of rings extending 20.3 mm from the center; 25.4 mm from the center; 30.5 mm from the center; and 35.6 mm from the center respectively. The coaxial LED located at the center and the two LEDs located away from the rings of LEDs are used to set the background lighting and calibrate the subject's retinal properties (e.g., reflectance and multiple scattering).

Figure 6D:
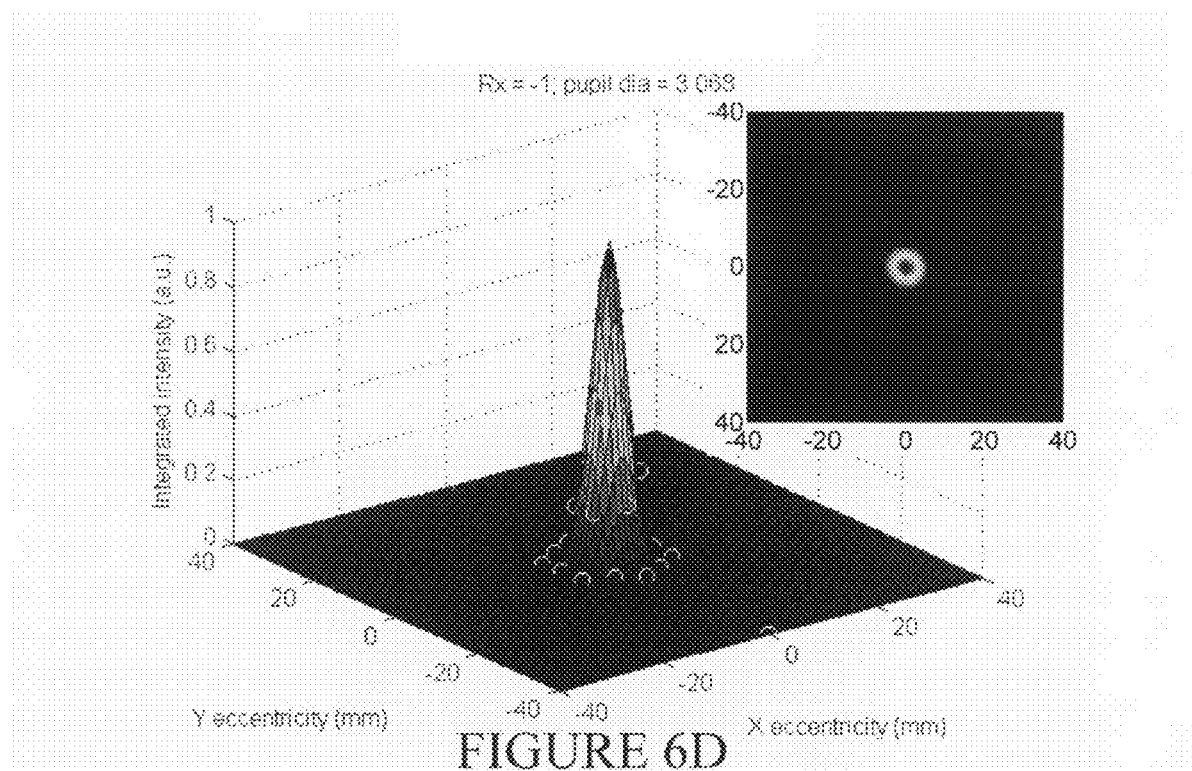
FIGS. 6D-6E are diagrams of three-dimensional bell-shape intensity profiles obtained using the irradiance arrangement of FIG. 6C by an embodiment of the APS system of FIG. 1.
Figure 6E:
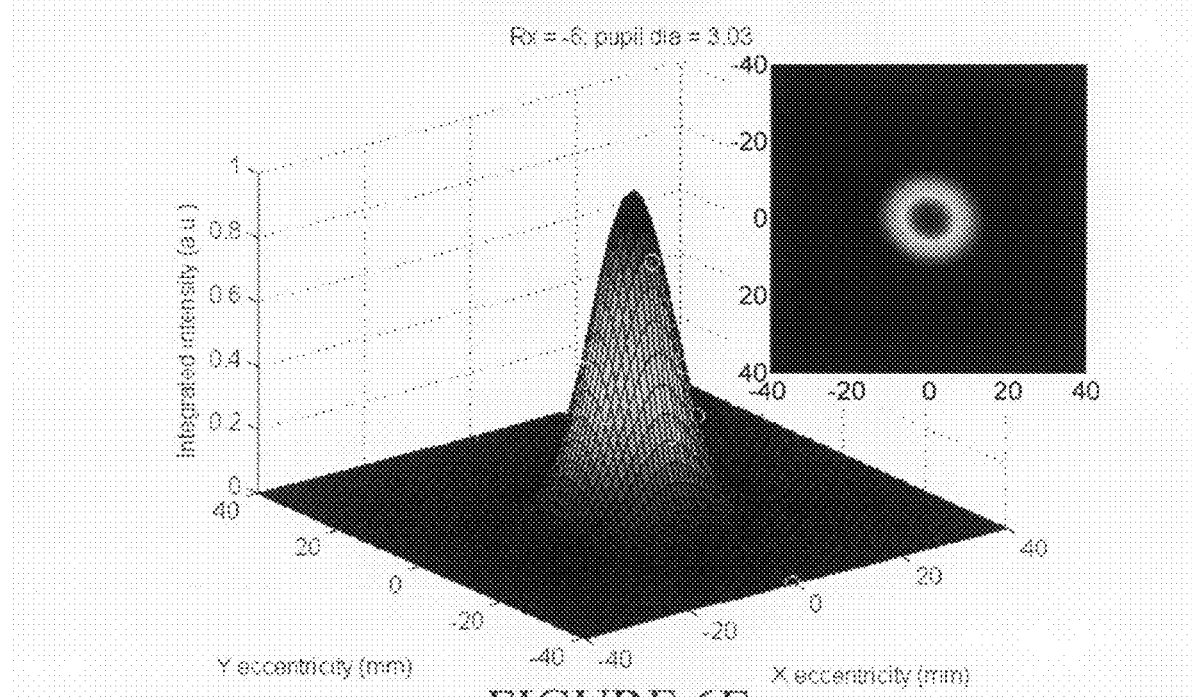

A three-dimensional bell-shape intensity profile (as shown in FIGS. 6D-6E) may then be obtained by the APS 100 and the data of these profiles can be used to conclude spherical (symmetric), cylindrical (asymmetric) refractive errors, and the astigmatism axis at the same time. In the profiles 620, 630 shown in FIGS. 6D-6E, the X and Y axes represent eccentricity in EPR and the Z axis represents the integrated intensity. This allows for two ocular meridians to be represented in a profile. In the diagram of FIG. 6D, a profile 620 for an eye having a −1 diopter refractive error is shown. Correspondingly, a profile 630 for an eye having a −6 diopter refractive error is shown in FIG. 6E.

B. Ocular Motility/Alignment

Another ocular screening procedure performed by some embodiments of the APS system 100 is an ocular motility and alignment test (which corresponds to item 320 in FIG. 4). In particular, an improved dynamic Hirschberg mechanism is used to test ocular motility and alignment for children 6 months and up under normal room light condition, in some embodiments. Generally, this automated test acquires binocular dynamic Purkinje images in order to identify strabismus and to provide an ocular alignment assessment.

Figure 7A:
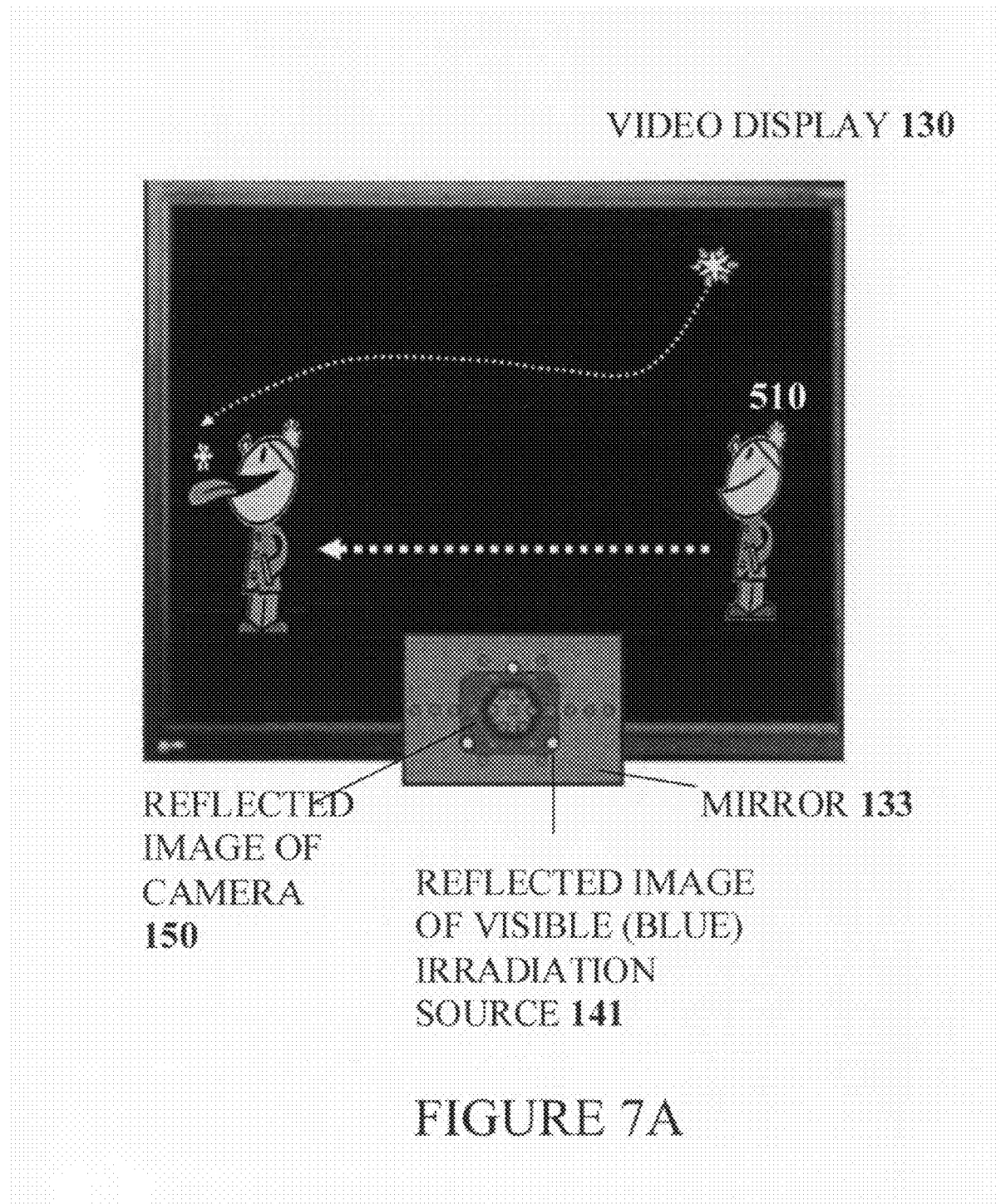
FIG. 7A is a diagram of an irradiation source and camera for a dynamic fixation and alignment test from the viewpoint of an examinee, in one embodiment of the APS system of FIG. 1.

In one example of the ocular alignment and motility test, an attracting target or figure for an examinee moves across a video screen 130 (as represented by the dotted white line, in FIG. 7A, as part of an animation feature). The attracting target 510 is displayed in red and green wavelengths and not blue, at a distance of ⅔ meter from the subject to provide a moving fixation target at a ⅔ meter distance. Room light environment 120 is regulated by the APS system 100 to reduce retinal reflex that may interfere with a Purkinje signal.

To examine ocular alignment along a predicted trajectory on a "convergence vs. gazing angle" lane, a sequence of binocular images is acquired through the dynamic Hirschberg test period. Any deviation (in time and space) from the normal path indicates a fixation or motility condition. For example, for a working distance of three feet, a 15 inch video screen 130 extends a 30 prism diopters range of test. For a closer working distance, the testing range is larger. Note that the test is valid even if the head of examinee is moving during the test.

The APS system 100 fires at least one blue, continuous, light source (e.g., a small, single, narrow-band LED light) throughout the test to prevent interference from a cornea reflection from the video screen 130 or other obstacles. The blue LED light source is located eccentrically from the optical axis of the digital camera, which is right below the video screen 130 to prevent an eye lash from blocking the Purkinje and iris image. The video camera 150 records binocular images from the examinee that are synchronized with moving targets displayed on the screen 130. The reflection of the continuous, blue LED defines a motion and moving trajectory of the gazing angle versus near constant convergence. From the viewpoint of the examinee through the mirror 133, a respective irradiation source and camera are arranged as shown in the lower portion of FIG. 7A.

From an acquired photoscreening image, the first Purkinje images of both eyes are used to determine the gazing angle and convergence of the examinee. Then, by plotting the result in an X-Y statistical plot featuring normal and strabismus cases (ET and XT) (obtained from many photoscreening images from many subjects (e.g., over 400)), the location of the plot for the examinee is observed to be in either a normal or abnormal region. Thus, a determination may be made about the ocular condition of the examinee and whether an ocular abnormality may exist.

The above approaches reference Hirschberg testing. A standard Hirschberg test applies an acceptable Hirschberg ratio (HR) and fovea location or angle (K) to derive an ocular gazing angle from photoscreening images. HR represents the corneal reflection movement (in mm) per unit of ocular angular rotation (in $\Delta$). The fovea angle (K) represents the angle between the visual axis and the pupillary axis. There is considerable population distribution scatter of the HR and K observed due to influences from subject differences. Therefore, a subject's actual HR and K values may differ significantly from the assumed values of HR and K based on population distributions.

Accordingly, in one embodiment, inter-subject variance of HR and K is taken into account by APS 100 to accurately measure the strabismic angle. One approach, among others, for measuring the strabismic angle determines an individual eye's Hirschberg ratio (HR) and fovea angle (K) through a simulated gazing trajectory as opposed to assuming values based on population averages. To determine a strabismus condition, ocular values and functional gazing trajectories of the subject's two eyes are compared to each other by APS 100.

For comparison, a clinical standard for testing strabismus is the Cover-Uncover test (also referred to VIP protocol). The first part of this test is the unilateral cover test. While wearing corrective eyewear, the subject is asked to focus on a letter of a distance eye chart. The optometrist or person administering the test then covers the subject's right eye while watching for a movement of the left eye. Upon removing the occluder, the optometrist waits for a few seconds to allow the subject's eyes to return to equilibrium and then proceeds by covering the left eye of the subject. If the eye not being covered moves to fixate the target (with both eyes open one eye is not aimed at the point of interest) that eye was not being used. This is referred to as a strabismus.

The alternating cover test is similar to the unilateral cover test but the main difference is that the occluder is switched from one eye to the next. If the eye just uncovered moves this is called a phoria. This means that in the resting position both eyes are not aimed at the target. Consequently, the subject must use effort to keep both eyes fixated on the target. This can cause eye strain and headaches. Prisms in the subject's spectacles or visual training may be required to correct the disorder.

A strabismus subject's eye movement depends on the fixating eye used to pursue a dynamic target trajectory. When viewing with a strabismic eye, the target tracking is achieved with a series of refixation saccades. The transition from smooth to saccadic pursuit is accompanied by a deviation of the eye movement from the target fixation path.

Accordingly, one embodiment of an approach for determining strabismus via the APS 100 uses a binocular orientation test. This binocular orientation test is performed under conditions of normal viewing and is uncontaminated by the eye measurement. An embodiment of APS 100 allows the test to be performed without alerting the subject being tested. During APS testing, binocular vision of the subject is significantly disturbed by occluding each eye of the subject during the fixation target's trajectory across the viewing zone. This allows the detection of latent strabismus.

One embodiment of APS 100 evaluates the binocular strabismic deviation angle and amblyopic response across a viewing range (binocular, monocular, and covered viewing zones) and not just at the center front. APS 100 determines HR, K, and the saccade scattering upon each eye in each of three viewing zones through binocular stimulation photographic trajectory of an individual examinee. APS 100 also evaluates the convergence in the three viewing zones to determine strabismic and amblyopic potential and condition.

Figure 7B:
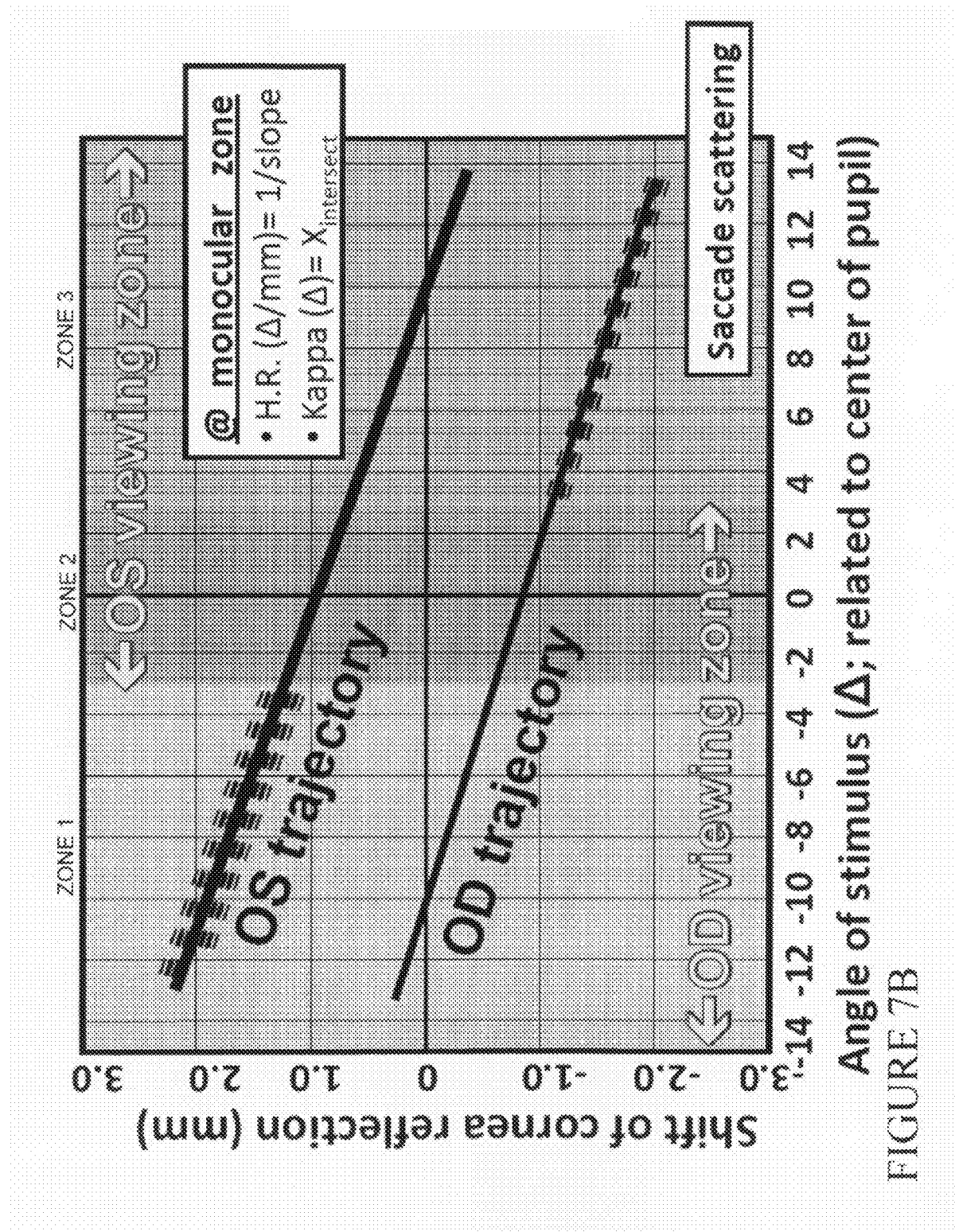
FIG. 7B is a diagram of a plot of a gazing trajectory for a subject's eye being measured by an embodiment of the APS system of FIG. 1.

As shown in FIG. 7B, a gazing trajectory for an eye being measured can be plotted across the three viewing zones ("Zone 1", "Zone 2", "Zone 3"). From the plotted trajectory, the Hirschberg ratio (HR) may be determined for an individual eye from the slope of the trajectory (e.g., in the monocular viewing zone when the other eye is occluded) by APS 100. Further, the fovea angle (K) may be determined by the APS 100 to be the intersection point of the trajectory at the X-axis, where the X-axis represents the angle of stimulus. Based on the individual measurements, an accurate gazing angle for the subject may then be determined from the Hirschberg ratio (HR) and fovea angle (K) by the APS 100.

Figure 7C:
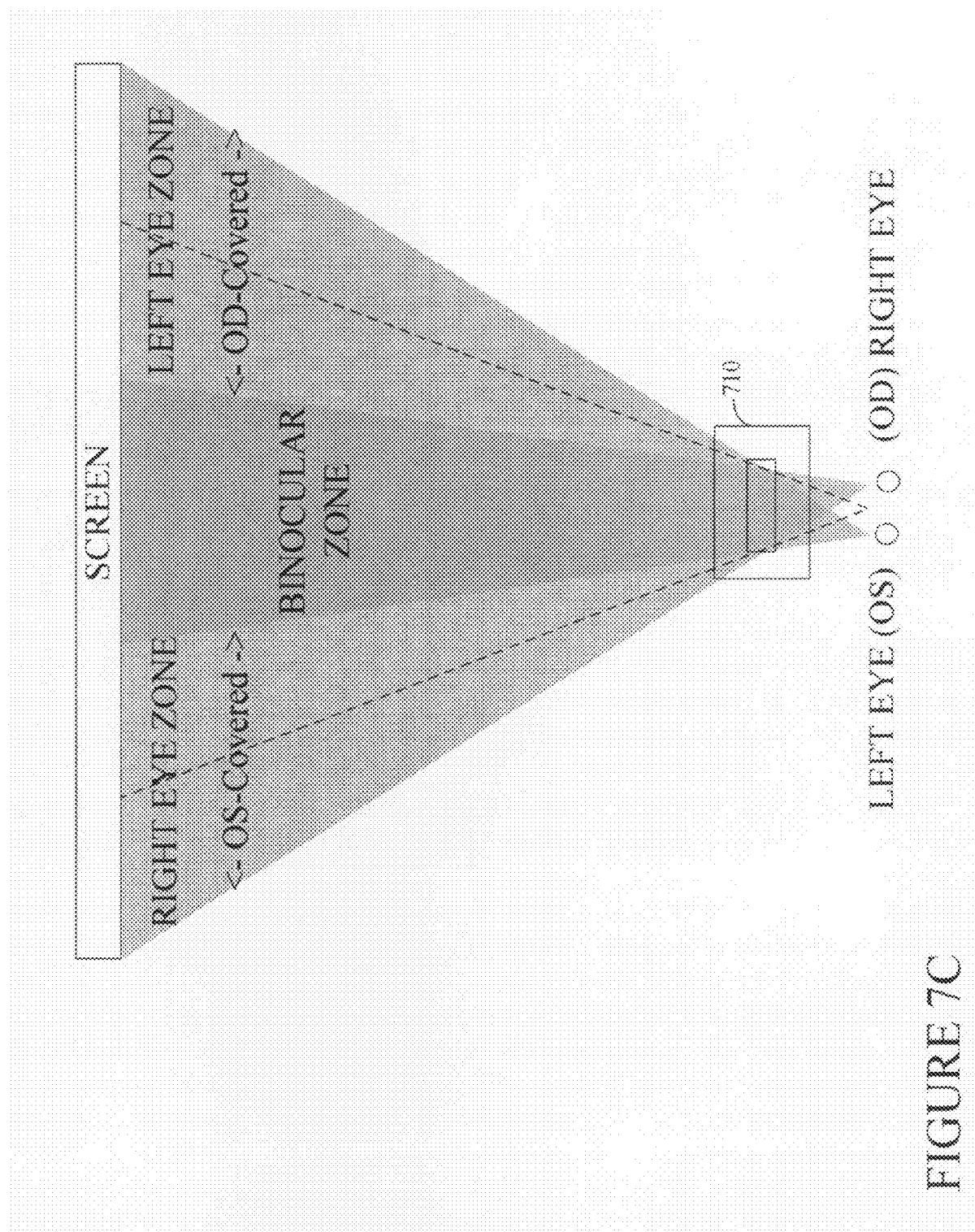
FIGS. 7C-7E are diagrams of various schemes to Cover-Uncover a subject's eyes during an eye examination using an embodiment of the APS system of FIG. 1.
Figure 7D:
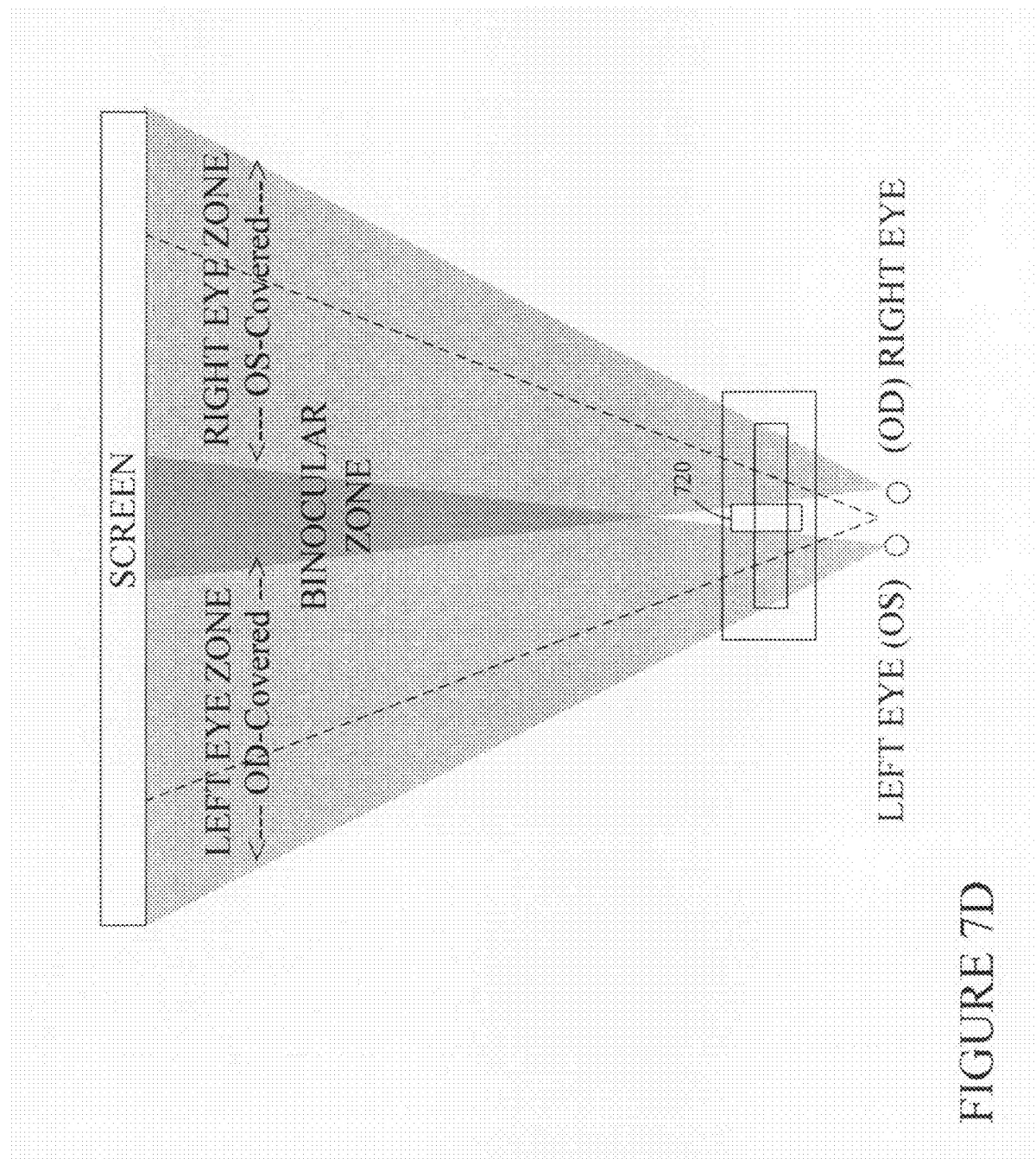
Figure 7E:
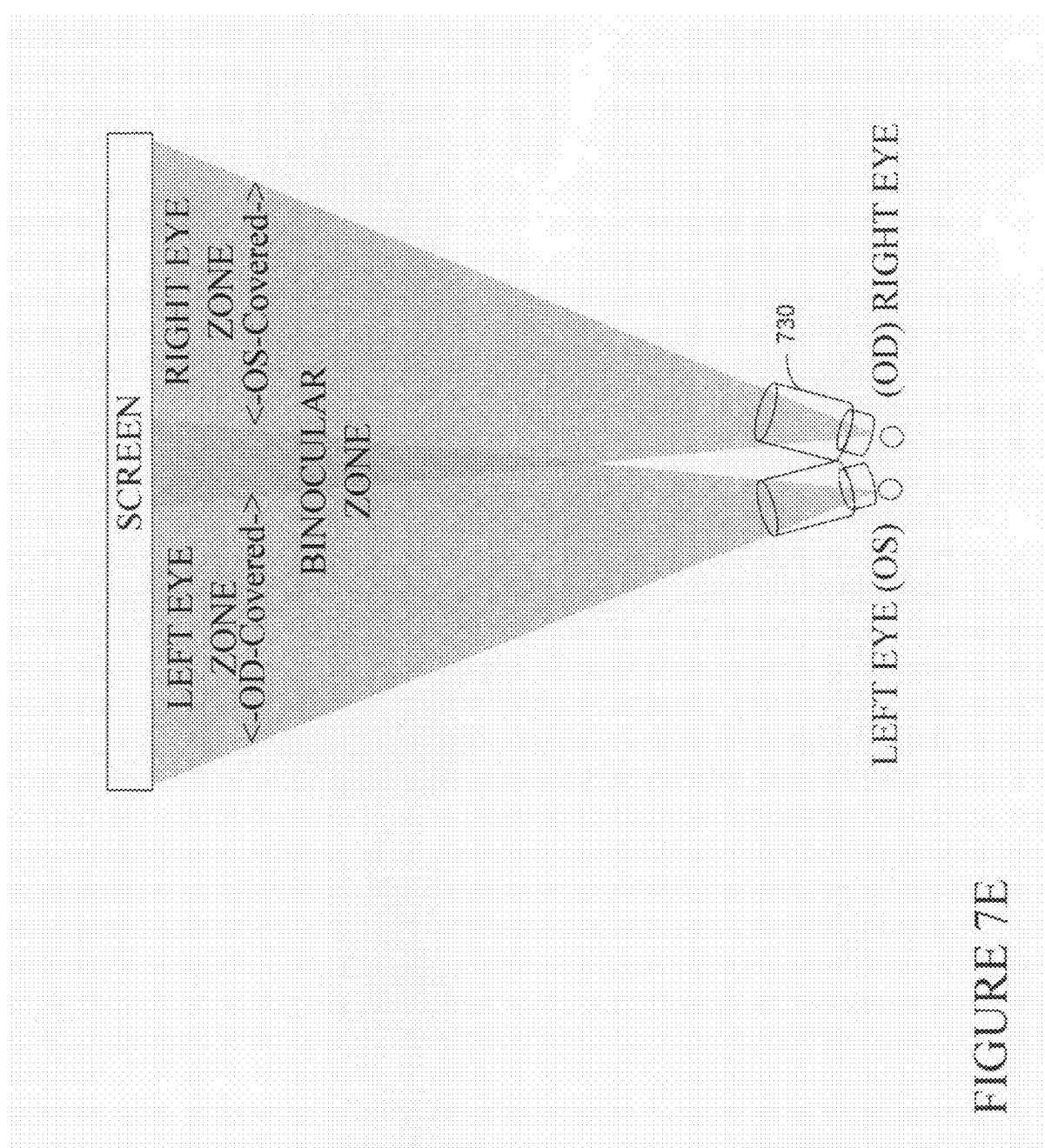

Different embodiments of APS 100 may utilize different methods of automatically covering-uncovering a subject's eyes without letting the subject become aware that one of his or her eyes is covered during a strabismus examination. For example, one method, among others, involves the APS 100 using a frame 710 to cover-uncover the subject's eyes for the three viewing zones (see FIG. 7C). The frame 710 provides a window that produces temple side boundaries through which the subject views a target. A second method involves the APS 100 using a nasal occluder 720 to cover-uncover the subject's eyes for three viewing zones (see FIG. 7D), where the occluder 720 produces a nasal-side boundary about which the subject views a target. A third method, among others, involves the APS 100 using binocular tubes 730 to cover-uncover the subject's eyes for three viewing zones (see FIG. 7E). The binocular tubes 740 produces a nasal-side boundary about which the subject views a target. By monitoring eye movement, difference may be identified from smooth pursuit eye movement as the target moves across the three viewing zones.

C. Tests for Ocular Media Clarity, Cornea Irregularity, and Retinal Tumor

An additional ocular screening procedure performed by some embodiments of the APS system 100 is a combined test for ocular media clarity, cornea irregularity, and retinal tumor screening (which corresponds to items 330 and 340 in FIG. 4). These tests are performed for all ages by evaluating the uniformity and distribution of the illumination and the spectrum distribution of the so-called "red-reflex."

An existing problem with conventional systems is that when the refractive error of the eye is either near emmetropic or extreme, the conventional eccentric photoscreening image appears "dark" in the pupil (the so-called dead zone). For example with a conventional device, a normal or mild refractive error may be detected and cataracts may be undetected. However, with additional coaxial and near-coaxial infrared images being generated at the same measurement and at the same time, as done by an embodiment of the APS system 100, cataracts (that resembles dark dots in the infrared image) are evident, although they would likely not be observed using any of current photoscreening devices.

Next, an additional test performed by some embodiments of the APS system 100 involves a cornea analysis to target cornea abnormality, keratoconus, and scars (which corresponds to item 330 in FIG. 4). With this test, one embodiment of the APS system 100 utilizes the infrared detection system and infrared LED irradiation pattern 142 of the setup used in the binocular refractive test to induce a dark environment that is not as bright as the environment used in the binocular refractive test. This is done, because large pupil sizes are required to cover a larger examination area of the cornea.

Further, retinal tumor measurement using a conventional eccentric photoscreening device is generally unsatisfactory. For example, when detecting abnormal retinal reflectance, which can indicate certain retinal tumors such as retinoblastoma, the light beam for the conventional eccentric photoscreening device reaches the retina under a tightly focused state. Thus, it covers a very small area of detection near the optical axis of the eye and often misses the diseased area, resulting in a needlessly high false negative outcome.

For the ocular opacity and cornea irregularity screenings (330) in APS 100, pulsed infrared irradiation is used and the irradiation arrangement is similar to the refraction measurement shown in FIG. 6. However, the environmental lighting should be dimmed so that the examinee's pupils are naturally dilated and the coverage of screening areas is sufficient. Based on both theoretical study and clinic trial, the observation of ocular opacities relies on the coaxial and near coaxial images. For the detection of cornea surface irregularity, on the other hand, the eccentric images provide a strong indication.

Figure 8:
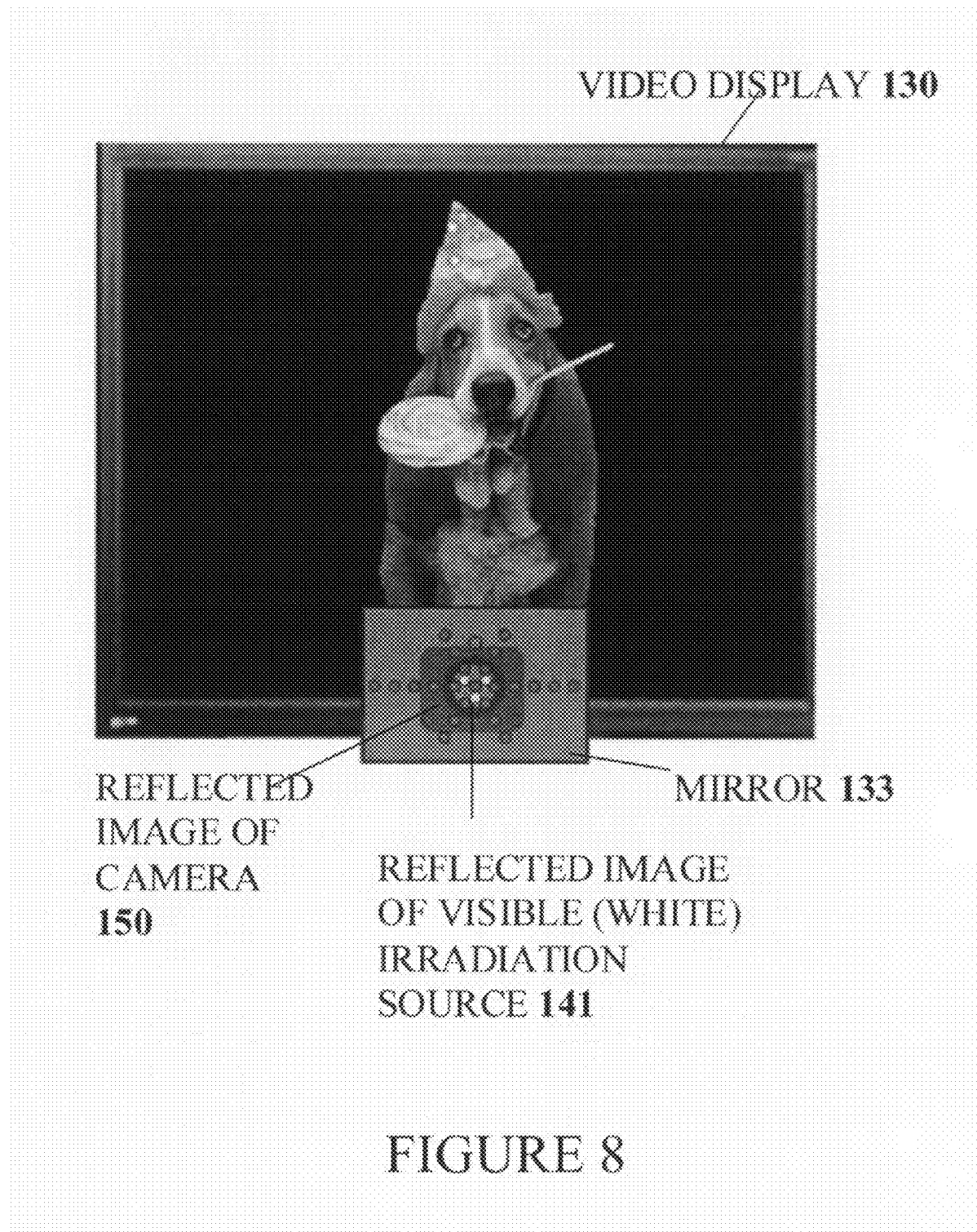
FIG. 8 is a diagram of an arrangement of an irradiation source and camera for corneal irregularity and optical opacity test from the viewpoint of the examinee, in one embodiment of the APS system of FIG. 1.

The retinal tumor screening (340) involves a broad-band irradiation source such as white LEDs. The irradiation should be near camera axis and the measurement requires the eyes in dilated condition as the first two. The lower middle part of FIG. 8 shows a possible spatial arrangement of the infrared and white irradiation sources for test items 330 and 340. With 30-60 Hz frame speed, the measurements for all three screenings are performed together within a fraction of a second. The white measurement 340 is performed as a single shot following the infrared measurement sequence. The video (animation) display should be dimmed (or shrink into the darkness) gradually just before the data acquisition sequence. Music/audio may be continuously played as if the video character is coming back to keep the examinee's attention in the dark. The infrared measurement is not visible to the examinee. The examinee sees only a single 'photo flash' for the 3 measurements including items 330 and 340. To cover a larger screening area on a retina tumor, the video program may guide a cooperative examinee to perform this test with more than one gazing angle.

For younger children who are difficult to cooperate, binocular measurements are guided by a programmed animated feature on the video screen 130, and the APS system 100 decreases intensity of the feature display within in a darkened room lighting condition as described. For cooperative examinees, rather than binocular, a monocular measurement may be performed at a closer distance to improve the spatial resolution and to improve the coverage and likelihood of detection. Any abnormal spectral reflectance or dark spots in either eye, asymmetry between the two pupils in size, shape, color, and brightness corresponds to a questionable ocular condition that generates a positive result by the APS system 100, as discussed below.

D. Color Blindness

A further test performed by some embodiments of the APS system 100 is a color blindness test (which corresponds to item 350 in FIG. 4). This test is generally performed for males over three years of age. Color blindness occurs in about 8%-12% of males of European origin and about one-half of 1% of females. Although there is no treatment for color blindness, once detected, guidance can be given to assist examinee's parents and teachers, etc. to deal with difficulties in the examinee's learning and daily lives. In general, the APS system 100 displays color pictures or images on video screen 130 that can be used to detect or indicate color blindness in examinees. For example, if an examinee is unable to distinguish certain colored features being displayed in a picture, then this is an indication of color blindness.

E. Extended Applications

Dynamic APS detection may also be applied to detect other types of ocular alignment problems, such as those involving schizophrenia; autism; post traumatic stress disorder; physical and emotional abuse, dyslexia, attention-deficit hyperactivity disorder (ADHD), etc. In one embodiment, the APS 100 directs the subject to visually pursue a target trajectory path in a similar manner as previously described. Subjects suffering from these types of ailments should have an irregular dynamic gazing angle trajectory (e.g., convergence and saccade and smooth pursue behavior) that is detectable by the APS 100 using infrared monitoring without disturbing the subject.

Auto-Analysis

From acquired photoscreening images from the screening procedures, the APS system 100 analyzes the images to attempt to detect ocular abnormalities by performing an auto-analysis process. Exemplary, one embodiment of the APS system 100 employs an auto-analysis process to perform real time interpretation of vision screening images on site.

As part of auto-analysis logic, the APS system 100 is configured to search for and report signs of abnormalities detected in acquired images. To detect signs of abnormalities, a variety of measurements may be analyzed, including: ocular divergence/gazing; pupil sizes/response; retinal reflex uniformity; retinal reflex intensity level; retinal reflex spectrum ratio; photorefractive gradient distribution; 2-eye correlation of all of the above; etc.

By and large, each measure has its high and/or low limits (threshold values) that define the region of normal and abnormal cases. Threshold values may be validated and calibrated based on clinical trial results.

As a further part of this process, the APS system 100 automatically classifies an image as a "positive" image indicating that the photoscreening image is deemed to show an ocular abnormality of some type or a "negative" image indicating that the photoscreening image is deemed to not show an ocular abnormality. To do so, the APS system 100 compares image data or information obtained from the image with statistical information for a variety of ocular conditions, both normal and abnormal, to determine whether the image data or information evinces normal or abnormal ocular condition(s). With an average processing time of less than a minute per examinee, auto-analysis process results can be categorized as: a positive group that may elicit a referral (e.g., direct referral to an ophthalmic professional); a negative group; and an uncertain group, where the photoscreening image(s) have produced unclear data. In one embodiment, photoscreening images from the uncertain group are referred to trained readers for additional analysis. In another embodiment, the examinee is advised of the uncertainty of the results and is advised to seek medical examination.

In one implementation of the auto-analysis process, over 90% of photoscreening images (normal & significant abnormal) are identified by the process with high confidence, and less than 10% of images are classified as being ambiguous or providing uncertain results. These types of results show a reduction of about 92% in the manpower for photoscreening image grading and electronic transmission in ocular evaluation as compared to conventional approaches, and this is taking into account the use of trained readers to analyze ambiguous results. By using alternative measures for ambiguous results, the reduction in manpower significantly improves further.

Accordingly, in FIG. 9, a flow chart is shown describing one embodiment of an auto-analysis procedure 900. First, in block 910, data acquisition is performed to obtain patient information and to acquire ocular images for subsequent analysis. Then, in block 920, image analysis is performed on the acquired ocular images. The type of analysis performed may depend upon the patient information acquired in the data acquisition step. Then, in block 930, a quality control step is performed to verify the data obtained in the captured images and whether the data is sufficient for subsequent analysis. If the data is not sufficient, then equipment setting and positioning, including examinee positioning, are checked and adjusted, and new data is obtained, as represented by block 940. Afterwards, the data acquisition step (910) is performed again. After image data has been qualified or deemed sufficient, the image data is analyzed to detect abnormalities within the image data, as shown in block 950. If the APS system 100 does not detect any abnormalities (e.g., a negative result), then the results are reported to the examinee, and the examinee may be released from the examination, as shown in block 960. If the APS system 100 does detect an abnormality (e.g., a positive result), then the examinee may receive a report on the abnormality and receive a referral to a medical professional for further examination and inspection, as shown in block 970. Otherwise, if the APS system 100 is unable to ascertain whether a positive or negative result is indicated by the image data, then the image data may be electronically transferred to a remote data reading center so that the image data can be analyzed by a trained reader. In some embodiments, alternatively, an uncertain result may be reported to the examinee without transfer of the image data, and the examinee may be advised to have a subsequent examination with a medical professional.

Next, various auto-analysis approaches are discussed with regard to different ocular screening procedures performed by logic of one embodiment of the APS system 100. For example, one implementation of an auto-analysis process analyzes photoscreening images using three distinct modules: a target finding module, an image quality assessment module, and abnormality identification module. First, the target finding module is discussed.

Figure 10:
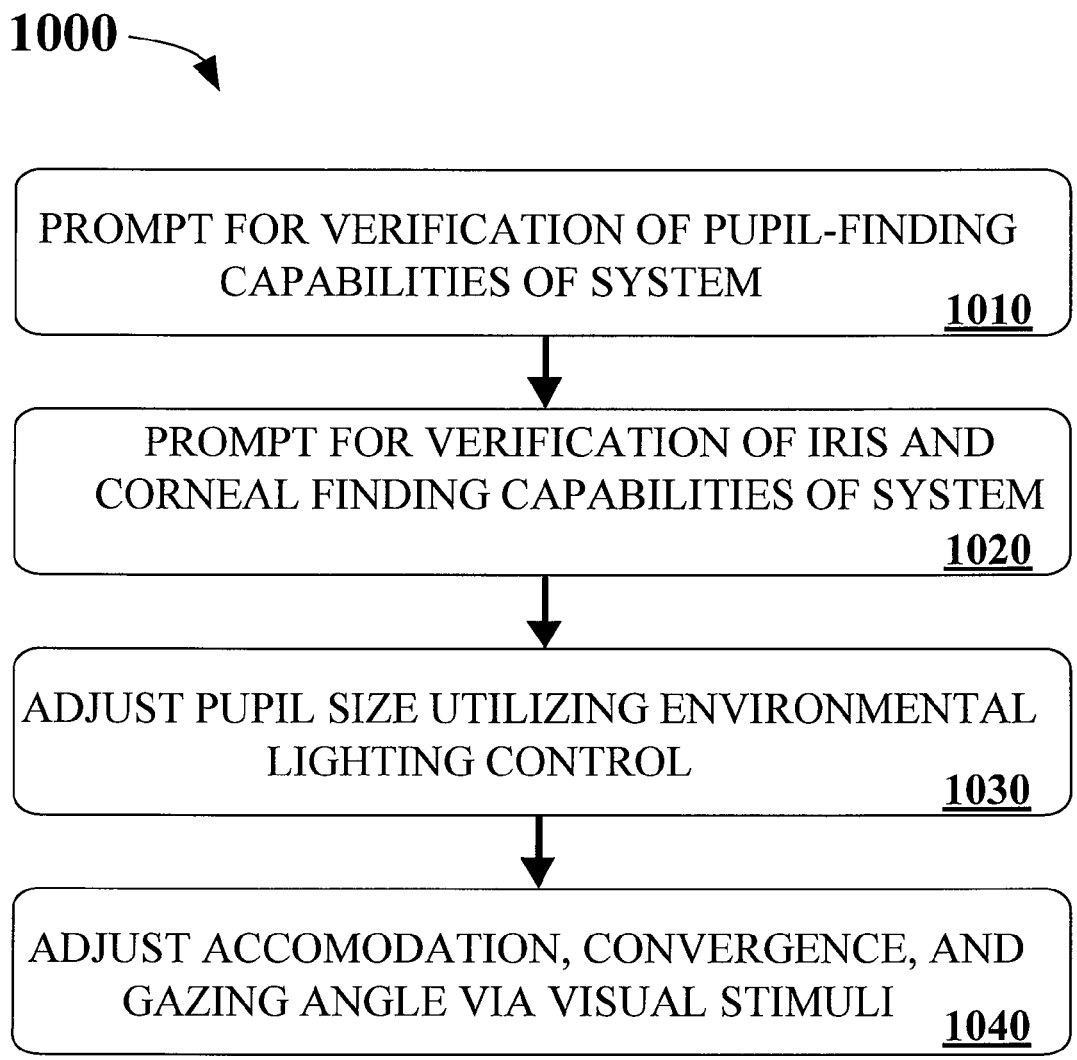
FIG. 10 is a flow chart describing one embodiment of a method performed by the target finding module of the APS system of FIG. 1.

The target finding module determines both the locations and sizes of the irises, pupils, and the centers of cornea reflections for each input photoscreening image. Referring now to FIG. 10, a flow chart describing one embodiment 1000 of a method performed by the target finding module of the APS system 100 is described. The method starts at block 1010, where an operator is prompted to provide verification of the pupil-finding capabilities of the infrared/visible camera 150, which are needed for refractive 310, ocular opacity 330, and retina tumor 340 tests. Then, in block 1020, the operator is prompted to provide verification of iris and corneal target-finding capabilities of the APS system 100 for assessments of ocular alignment and motility. Accordingly, control of pupil size by programmed variations of room or environmental lighting 120 may be performed, as shown in block 1030. Visual stimuli (e.g., video animation) are used to control accommodation, convergence, and gazing angle of the examinee, in block 1040.

Figure 11:
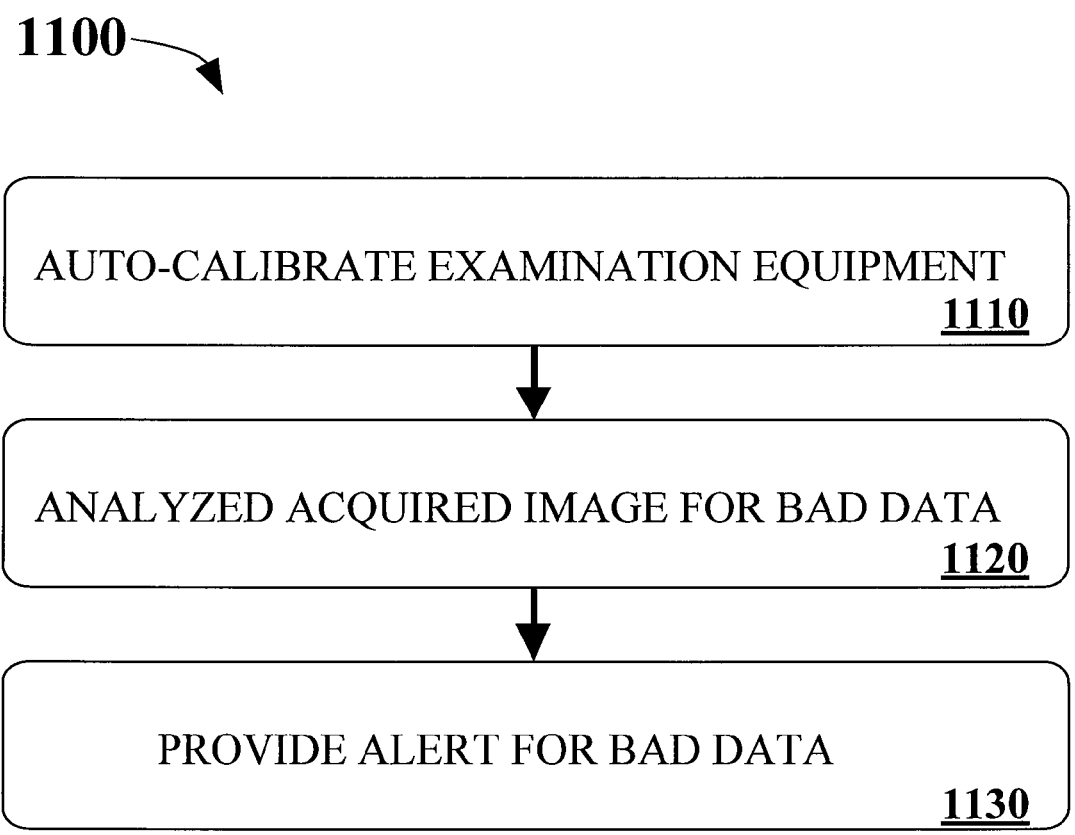
FIG. 11 is a flow chart of one embodiment of a method implemented by an image quality assessment module of one embodiment of the APS system of FIG. 1.

Next, with operation of the image quality assessment module, an index of the quality of each of the six fitted targets (2 pupils, 2 iris, 2 cornea reflections) is calculated. The fitting indices are normalized to the maximum possible values that occur for a perfect fitting of well-focused images of properly aligned examinees. Referring now to FIG. 11, a flow chart of one embodiment 1100 of a method implemented by the image quality assessment module is described. First, in block 1110, auto-calibration of examination equipment is performed. For example, the lens of respective camera 150 is automatically adjusted to frame the region of the eye(s) of an examinee that is of interest for a particular test. Further, room/environmental lighting 120 is automatically adjusted to the correct setting for obtaining a desired ocular response. In particular, image intensity is calibrated and normalize to offset effects from environmental illumination variation and result noise level; light source intensity is adjusted to counteract effects from aging and detection gain; and individual retinal reflectance properties are calibrated to attempt to ensure the best image quality.

Next, in block 1120, after a photoscreening image is captured, the image is analyzed for bad image data and technique faults (e.g., improper equipment setup) to ensure quality control. For example, within a captured image, one or more of the following regions are attempted to be determined by the APS system: iris locations; cornea reflections locations; pupil locations; and pupil diameters. Each has its index of goodness-of-fitting, and the APS system 100 attempts to identify off-focused images and images with hair, eye lash, eye lids that block pupils, both eyes looking away from camera, very small pupil(s), etc.

For defocused photoscreening images or for partially truncated irises or pupils (e.g., resulting from squinted eyes or eyes partially blocked by hair or hand), the fitting index ranges from zero to one in order of increasing quality of the image. This quality control index provides either an alert (1130) during the analysis of an unreadable image or a measure of the reliability of analysis result(s).

Signs of abnormalities detected by the APS system 100 are targeted to reveal ocular conditions, including the following: strabismus; anisocoria; ptosis; optical opacities; tumor; refractive errors; anisometropia; amblyogenic conditions; keratoconus; color blindness; etc. In one embodiment, the abnormality identification module includes three elements: a strabismus module that analyzes the locations of the corneal reflections, an eye-correlation module that compares differences of retinal reflex between two eyes, and a single-eye module that examines abnormalities of each eye. The measured values and any consequent referral decisions are affected by the parameter distribution functions of each module, or filter.

To illustrate, FIG. 12 shows a two-outcome frequency distribution function for a measured parameter by the APS system 100. In this example, the frequency distribution displays positive and negative functions, respectively, that represent measured values corresponding to positive criteria (that may elicit a referral) and negative criteria (that signifies a healthy condition). The cases that satisfy the positive criteria exhibit a fraction of false positive results and similarly for the negative cases. In such embodiments, where it is an objective to obtain a two-parameter outcome, a "cut-parameter" is utilized to discriminate positive and negative results.

In alternative embodiments, where a three-outcome distribution (e.g., referral or positive, non-referral or negative, and undetermined), two cut-parameters are utilized (e.g., T1 and T2). FIG. 12 shows such a case for the single-peak distribution of both positive and negative results. Accordingly, the locations of two cut-parameters are selected to obtain simultaneously high predictive values of the positive and negative outcomes and acceptable values of the undetermined outcomes.

The final grading report determined by the APS system 100 is based upon the combined results of all three modules (strabismus, eye-correlation, and single-eye). For photoscreening images that are in a negative distribution for all three modules, negative reports result. For images that are in a positive distribution for one or more modules/filters, positive grading results. For the remainder, uncertain results are determined and transfer of image data to trained readers may be recommended.

A more complex distribution is shown in FIG. 13 in which it features an asymmetric bimodal positive distribution and a single mode negative distribution. In this case, high- and low-thresholds or cut-parameters are used (e.g., T1, T2, T3, T4), as shown in FIG. 13. Examples of tests that may produce results with such distributions are the convergence value of strabismus and the refractive status of an eye for which the distribution peaks of abnormal response appear on both sides of the distribution function of normal response.

Figure 14:
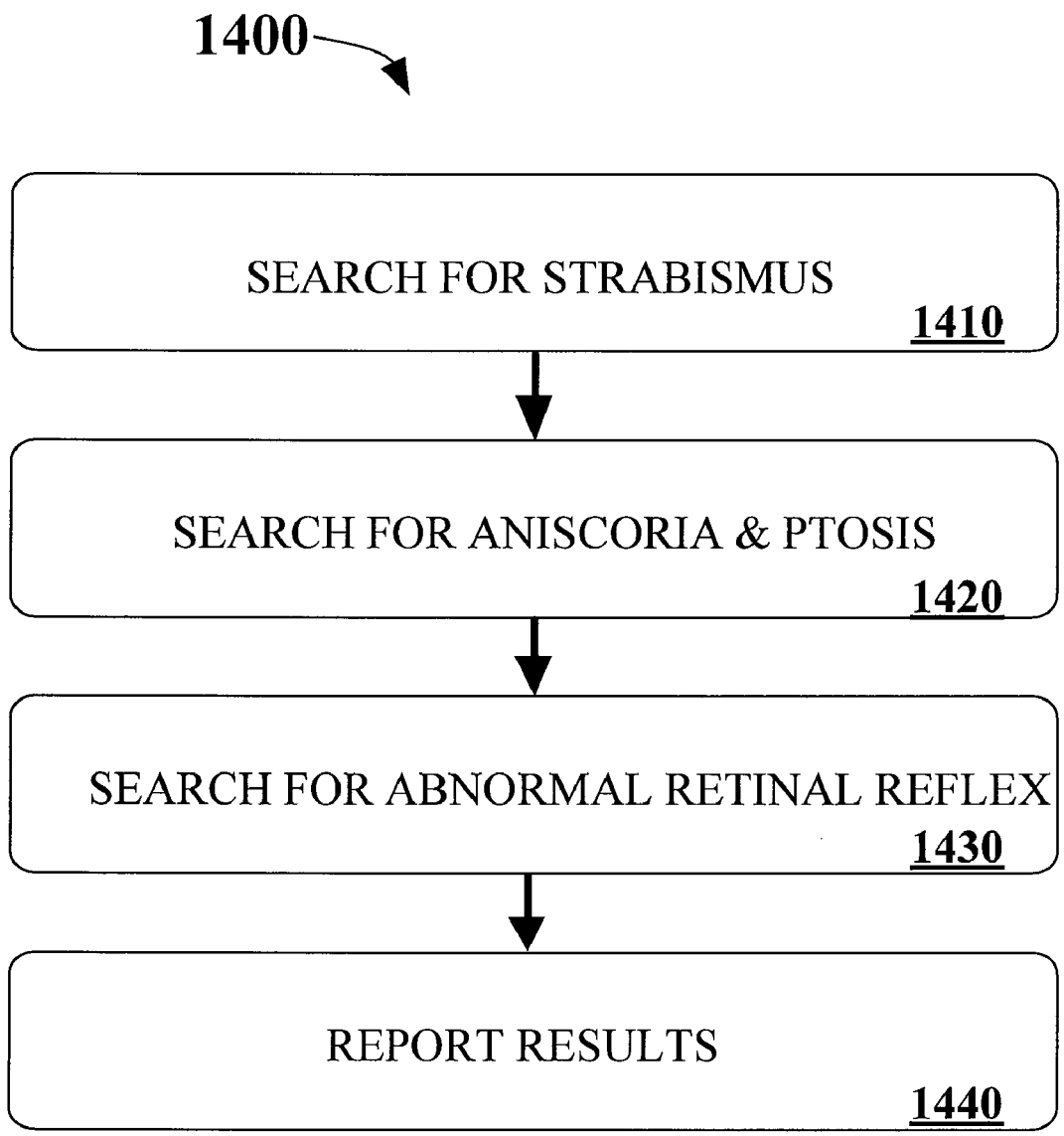
FIG. 14 is a flow chart describing one embodiment of a method implemented by the APS system of FIG. 1.

By and large, in one embodiment, an abnormality module performs the method 1400 represented by the flow chart of FIG. 14. In no particular order, the abnormality module performs (1410) a search for abnormal ocular alignment and movement by analyzing photoscreening images. Further, the abnormality module performs (1420) a search for anisocoria and a search (1430) for abnormal retinal reflex in analyzing photoscreening images. Results of the searches are then reported (1440).

Referring now to the individual sub-modules of the abnormality module, the strabismus module coordinates the center locations of the two irises in a binocular image. The inter-ocular distance and head-tilt angle are also calculated. Using the Hirschberg method, the related corneal reflection positions give the examinee's convergence and fixation or gazing angle, which are two variables that define the deviation of eye alignment (e.g., esotropia (ET), exotropia (XT), and normal cases) in the analysis process. Accordingly, from these calculations, they are compared with regions of normal, abnormal, and uncertain results to indicate whether the captured image shows an abnormality related to strabismus, as previously discussed. In some embodiments, hypertropic conditions are also analyzed.

The eye-correlation module and single-eye module are used to examine the abnormalities in the pupil area of the image or so called retinal reflex signal. Via the eye-correlation module, a search for anisocoria and ptosis is performed by examining pupil response and eliminating data with significant difference in pupil diameter and ocular appearance. In particular, each pupil image is separated into red (including infrared), green, and blue panels for all analyses by the APS system 100. The eye-correlation module compares the difference between a left and right eye in each of the following areas: intensity; uniformity (intensity deviation); intensity (along the eccentricity direction) gradient; and R, G, B spectrum ratios. Regions of interest are then compared against predetermined thresholds and regions of normal, abnormal, and uncertain results.

Also, abnormal signs may be searched in each eye. Accordingly, a single eye module is used to separate R (red), G (green), B (blue) images and then separate a pupil image in a direction along camera-light alignment (eccentricity directions). Each sub-area is evaluated with respect to intensity; uniformity (intensity deviation); intensity (vertical) gradient; R, G, B spectrum ratios. Regions of interest are compared against predetermined thresholds and regions of normal, abnormal, and uncertain results. For APS 100, the quantitative refraction analysis is further performed through the ratios of total reflex intensity between images.

Figure 15:
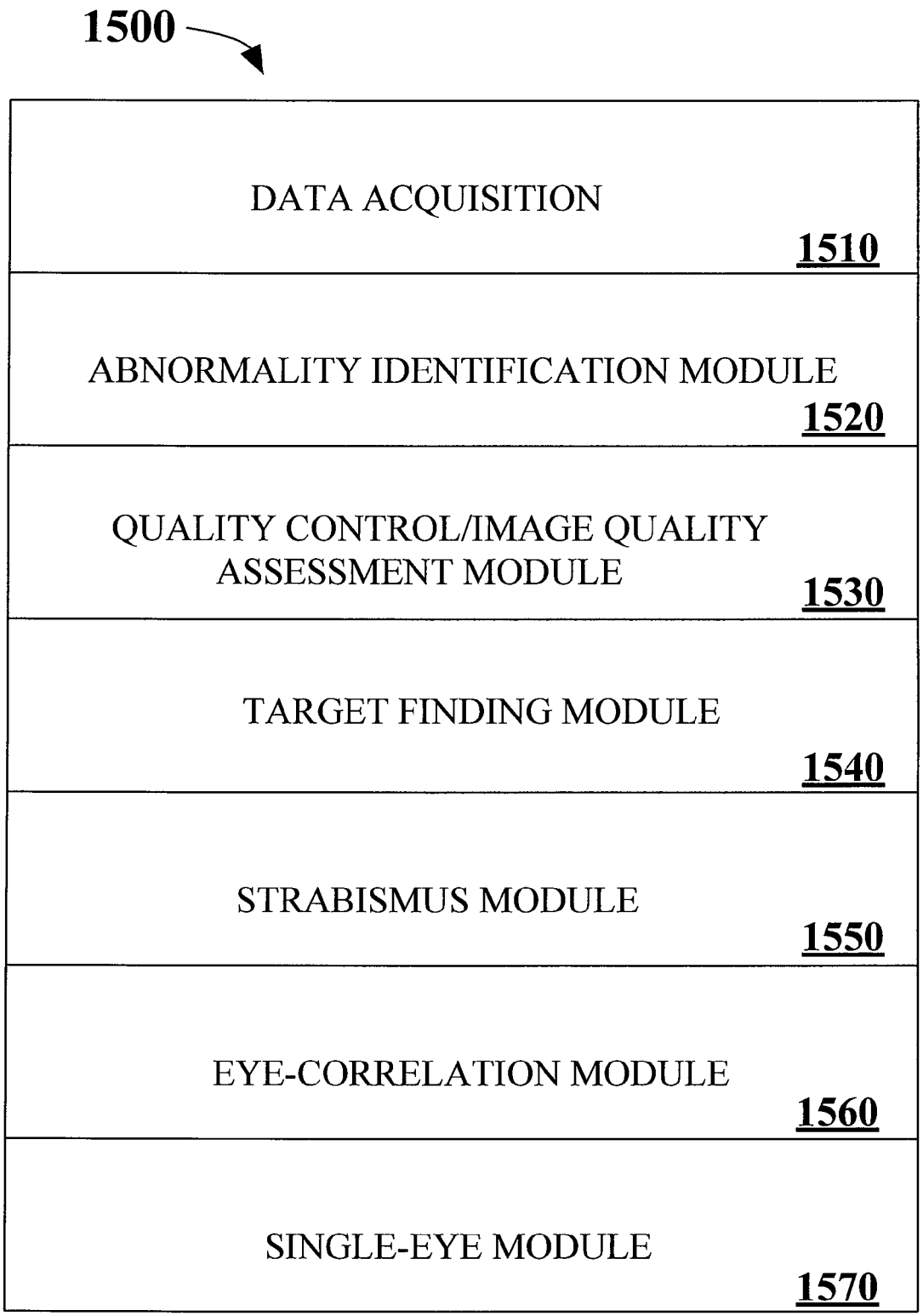
FIG. 15 is a block diagram representing logic components for one embodiment of the APS system of FIG. 1.

For illustrative purposes, FIG. 15 represents one embodiment of components of logic for the APS system 100. As shown, APS logic 1500 includes the following components: data acquisition module 1510, abnormality identification module 1520, quality control or image quality assessment module 1530, target finding module 1540, strabismus module 1550, eye-correlation module 1560, and single-eye module 1570, as has been previously discussed. Additionally, APS logic may include additionally functionality (such as computer control 110) and different embodiments may even include different functionality subsets. Thus, embodiments of the present disclosure are not limited to the representation of FIG. 15.

As part of the auto-analysis process for one embodiment, a computer schematic eye-model is used that reproduces optical characteristics of a human eye, including refractive errors and customization. Although many successful eye models are available today, these models are constructed for the emmetropic (refractive-error free) adult condition without pathology. In such conventional models, average measured values are adopted for all ocular optical parameters. There is no specific gender, age, or race characteristics associated with these conventional models. Further, the conventional eye models fail to describe parameter variations in the population. Such information is particularly important in applications related to public health.

Accordingly, one embodiment of an eye-model of the present disclosure incorporates refractive errors, the most prevalent vision defect in population. Hence, the correlation between refractive errors of the eyes and ocular parameters (the ocular axial lengths, cornea curvatures, and intraocular powers in particular) are featured in the eye model. As such, the eye model describes refractive error with variations of cornea curvature, axial length, and intraocular power simultaneously and considers the distributions of these parameters' variations in the examinee's group, such as a group of young adults in a certain age range.

Advantageously, the Adaptive Photoscreening System (APS) 100, according to one embodiment of the present disclosure, employs multiple light sources 141, 142 with programmed sequenced irradiation of the eyes in the visible (VIS) to near-infrared (NIR) regions and both still frame and video digital camera 150 (both infrared and color) to perform: binocular measurements of the refractive errors, detection of strabismus and amblyopia, cataracts or optical opacity, ptosis, nystagamus, and specific corneal abnormalities. Further, APS 100 increases the retinal area of observation to enhance the likelihood of the observation of certain types of retinal tumors as manifested by abnormal retinal reflectance. In addition, tests performed by the APS system 100 are age-specific and multi-functional with respect to abnormality detection and satisfies the current recommended guideline from the American Academy of Opthalmology (AAO 2003). AAP and other organizations also give the similar recommendations. It is noted that for the majority of tests, objective screening is recommended.

Specifically, guidelines have been proposed stating that refractive error should be supplemented, for example, by assessments of strabismus, motility, and inspection for ocular optical opacity and retinoblastoma. Binocular, objective measurements, as implemented by the APS system 100, fulfill these requirements in a mass screening environment. To satisfy these requirements and the desire to perform large population screening applications using electronic transfer of results, embodiments of the APS system 100 enable the testing of a range of ocular functions and to offer the significant potential for telemedicine applications.

Embodiments of the APS system 100 offer potential for application to the medically under-served population of the U.S. and to developing nations of the world that lack the resident medical expertise and resources, in addition to general pediatric screening. The versatile and cost-effective design of the APS 100 allows its deployment and use by trained but non-medical operators to achieve the desired public health screening of children. With simple modular modifications, APS 100 provides a less mobile but more capable vision evaluation system that is suitable for pediatric clinics.

Note that the set of examinations performed by embodiments of the APS system 100 satisfy the Eye Examination Guidelines of the American Academy of Pediatric Ophthalmologists (AAPO) and AAP announced in 2002 and 2003 and are also applicable for older age groups. Further, embodiments of the APS system 100 are characterized by transportability (so that the evaluation is transportable, e.g., can be taken to children); simple examination procedures (which is beneficial for pre-school children); simplicity of operation; comparative low cost equipment/instrumentation; and completeness and accuracy of ocular assessments.

Advantageously, in accordance with one embodiment of the APS system, an uncertainty of less than 0.5 diopter for measurement of refraction (conventional EPR systems have a standard error of ~+−2.0 diopters) can be achieved and used to accurately identify opacities.

Further, with the APS system 100, light sources are wavelength dependent (e.g., range from quasi-blue to near infrared), and individual ocular aberrations are able to be isolated, based on wavelength ranges, and measure refractive content and opacity of the eye which may be wavelength dependent, such as cataracts, floaters, retinal tumors, keratoconus, corneal scarring, corneal ulcers, etc.

Further, embodiments of the APS system 100 utilize pulsed light sources, such as a series of LEDs, among others, where each light source is pulsed on for a certain period of time. The refractive measurement may be then made in the infrared region because the eye does not respond to infrared light and the pupil does not contract or expand, so a refractive measurement can be made at leisure with a pulsed source without altering condition of the eye (e.g., performing refractive measurements utilizing a sequent infrared radiation under a lighting environment that is suitable for near distance visual activities, such as reading). When measurements are made within the visible range, pupillary responses are existent and are taken into account. Accordingly, the sequence of measurement, such as the order at which wavelength-dependent light sources are activated, may be configured to ameliorate or lessen pupillary response.

Also, as described, photoscreening techniques of one embodiment of APS 100 provides radiant stimuli (e.g., irradiation sources 141, 142) and detectors 142, 150 that span the broad spectrum from visible wavelengths (e.g., RGB) to near infrared; utilizes multiple-light-source stimuli 141, 142 in a two-dimensional array to cover various source-detector angles and eccentricities; and provides digital multiple-shot image detectors 150 (rather than a typical single snap-shot camera). This three-fold characteristic enables APS 100 to extract accurate ocular parameters by decoupling the mixed, or ambiguous, information that is often obtained using current devices.

In contrast to a typical photoscreening image, where only partial ocular information is collected by a camera depending on its aperture and its angular location relative to a light source, one embodiment of APS 100 obtains improved accuracy and enhanced information content by using a time-sequence of light sources 141, 142 of various spectral signatures and digital camera detection at two angular locations of the returning spectral radiance.

Advantageously, one embodiment of APS 100 (1) adjusts room light environment 120 to control the examinee's pupil size, (2) uses an optical beam splitter to combine illumination and detection spaces, (3) uses an infrared photorefraction (PR) image to self-calibrate retinal differences, (4) uses a spatially integrated intensity profile to obtain refractive error (thereby discarding the ambiguous crescent interpretation), (5) uses multiple-angle illuminations and eccentricities that definitively determines astigmatism, and (6) uses centrosymmetric illumination that corrects the gazing angle effect.

One advantage of the above described embodiment(s) is that it is non-mydriatic and, therefore, requires no pupil dilation using drugs.

Figure 16:
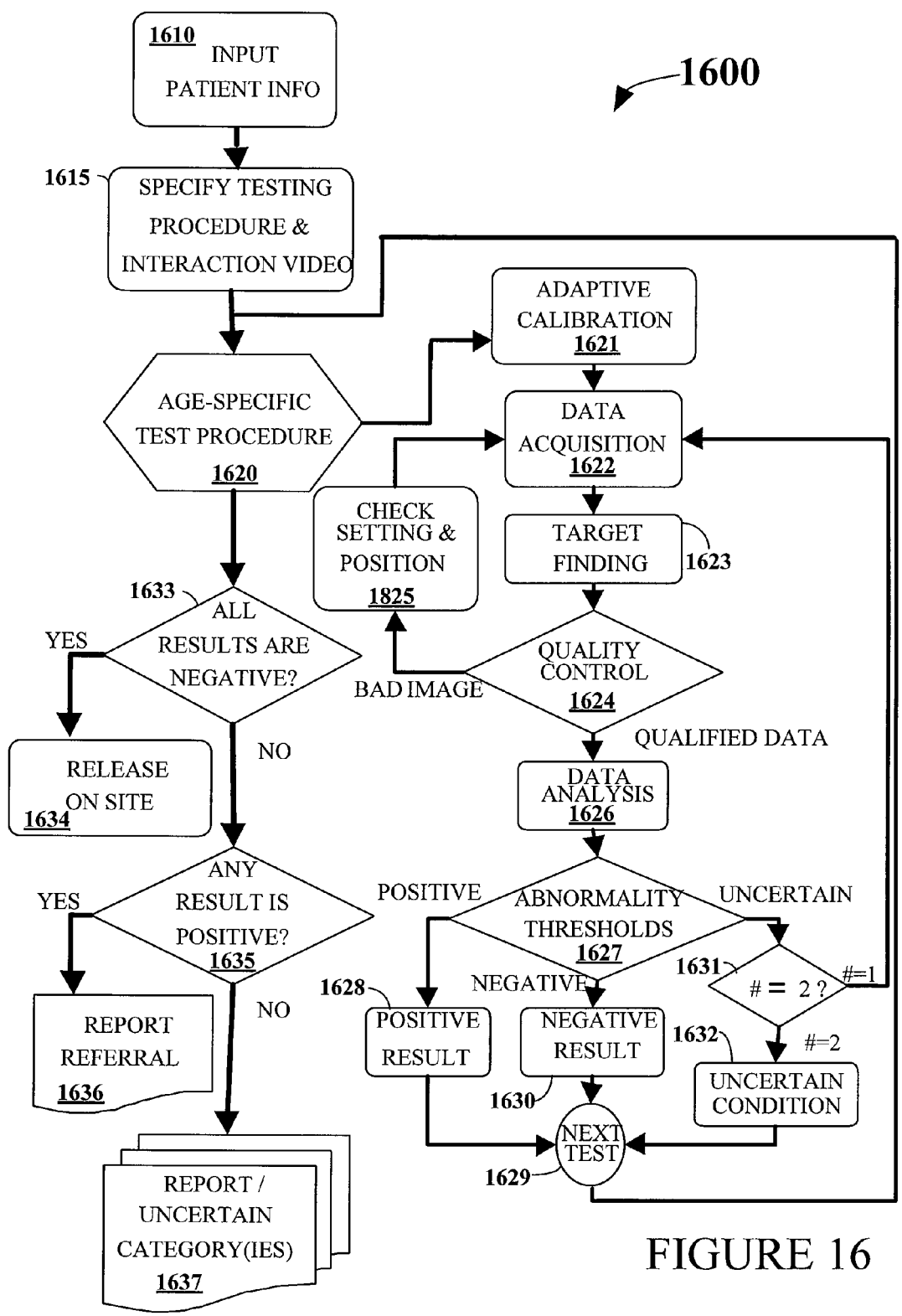
FIG. 16 is a flow chart describing one embodiment of a screening procedure utilizing one embodiment of the APS system of FIG. 1.

Next, FIG. 16 is a flow chart describing one embodiment of a screening procedure utilizing the APS system 100. In a first step, input patient data (e.g., data (date/year of birth, gender, race, reside area, ID code, etc.) is acquired (1610). This information is used to determine which tests are to be performed and in the data analysis to be performed later, the information is used to determine which ocular calibration parameters are to be used. Accordingly, the testing procedure is specified (1615) along with an interaction video feature or game that is used for the selected testing procedure.

The APS system 100 then implements (1620) and performs the age-specific test sequence, where the test sequence is also gender-specific, in some embodiments. Depending on age and gender of the examinee, two to five tests may be performed, where the data is analyzed according to age and race, in some embodiments.

Each of these tests may include the following steps: adaptive calibration (1621) of ocular positioning (e.g., a video feature or game will end if the ocular positioning is not acceptable), environmental lighting to adapt to the individual pupil response to light, and radiance of infrared light sources to be use during the measurements (adapt to the retinal reflectance of the individual). Then, data acquisition is performed (1622) including the steps of target finding (1623) and quality control (1624). If the data acquired is not above a required quality, the step goes back to step 1622 after checking (1625) test settings and positioning of the examinee. Otherwise, while the APS system 100 is analyzing (1626) data, the calibration of the next test proceeds.

From data analysis (1626), results of the testing procedures are compared against abnormality thresholds (1627). If a positive result is determined (1628), the determination is logged by the APS system 100. Then, the next screening procedure or test is performed (1629). Likewise, if a negative result is determined (1630), the result is logged by the system and the next test is performed (1629).

If an uncertain result is determined (1631), step 1623 is repeated for a first instance. However, if two uncertain results occur, then an uncertain result or condition is determined (1632) and logged by the system. The next test then commences (1629).

If all the results to the screening procedures have been logged as being negative (1633), then the examinee is released (1634) from the examination. Accordingly, if any results are positive (1635), a referral is reported (1636). Further, any uncertain results or categories are reported (1637). In some embodiments, screening results may be provided within a minute after the test procedure. Also, some embodiments of the APS 100 tailor the screening methods and analysis algorithms to fit the needs of the individual.

Components of embodiments of the present disclosure can be implemented in hardware, software, firmware, or a combination thereof. For example, in one embodiment, the APS logic is implemented in software or firmware that is stored in a memory and that is executed by a suitable instruction execution system. If implemented in hardware, as in an alternative embodiment, the APS logic can be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array (s) (PGA), a field programmable gate array (FPGA), etc.

When implemented in software, components of the APS system 100 can be stored on any computer readable medium for use by or in connection with any computer related system or method. In the context of this document, a computer readable medium is an electronic, magnetic, optical, or other physical device or means that can contain or store a computer program for use by or in connection with a computer related system or method. In the context of this document, a "computer-readable medium" can be any means that can store, communicate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

Any process descriptions or blocks in flow charts should be understood as representing modules, segments, or portions of code which include one or more executable instructions for implementing specific logical functions or steps in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

It should be emphasized that the above-described embodiments of the present disclosure are merely possible examples of implementations, merely set forth for a clear understanding of the principles of the disclosure. Many variations and modifications may be made to the above-described embodiment(s) of the disclosure without departing substantially from the spirit and principles of the present disclosure. All such modifications and variations are intended to be included herein within the scope of this p disclosure.

Therefore, having thus described the invention, at least the following is claimed:

1. A system of automatic computer analysis for photoscreening system that comprises:
    a strabismus module that analyzes ocular fixation and motility;
    a single-eye module that analyzes abnormalities of each single eye; and
    an eye-correlation module that compares differences of retinal reflex between two eyes, wherein the strabismus module determines an examinee's convergence and fixation angle; and compares the examinee's convergence and fixation angle with regions of normal, abnormal, and uncertain results to indicate whether a captured ocular image shows an abnormality related to strabismus.

2. A system of automatic computer analysis for photoscreening system that comprises:
    a strabismus module that analyzes ocular fixation and motility;
    a single-eye module that analyzes abnormalities of each single eye; and
    an eye-correlation module that compares differences of retinal reflex between two eyes, wherein the single-eye module analyzes retinal reflex of each eye in each of the following areas: intensity spatial distribution and gradient of each spectral region of interest; uniformity; and spectral distribution; and compares signals at regions of interest against predetermined thresholds.

3. The system of claim 2, wherein each pupil image is separated into red, green and blue panels.

4. The system of claim 2, wherein the intensity gradient is along an eccentricity direction of a camera-light alignment.

5. A system of automatic computer analysis for photoscreening system that comprises:
    a strabismus module that analyzes ocular fixation and motility;
    a single-eye module that analyzes abnormalities of each single eye; and
    an eye-correlation module that compares differences of retinal reflex between two eyes, wherein the eye-correlation module compares difference between a left and right eye in each of the following areas: intensity of spectral region of interest; uniformity; intensity gradient and distribution; and spectrum ratios, regions of interest being compared against predetermined thresholds.

6. The system of claim 5, wherein the spectrum ratios include red, green and blue spectrum ratios.

7. The system of claim 5, wherein the intensity gradient is along an eccentricity direction of a camera-light alignment.

8. A method of performing optical opacity examination of an eye comprising:

utilizing a photoscreening technique employing co-axial infrared radiation under a dimmed lighting environment to screen the eye for optical opacity.

9. A method of performing cornea and keratoconus examination comprising:
utilizing an eccentric photoscreening technique with a sequent pulsed infrared radiation under a dimmed lighting environment to obtain sequenced images to screen for cornea abnormality and keratoconus.

10. A method of performing retinal examination comprising:
utilizing a co-axial photoscreening method providing co-axial irradiation to illuminate a subject with a broad band spectral radiation and an image detection system that detects signals in multiple wavelength regions under a dimmed lighting environment generated by the co-axial irradiation to screen for retinal abnormality.

11. A method of determining ocular spherical and cylindrical refractive errors from a video photoscreening system comprising:
utilizing a ratio of integrated intensities obtained from multiple images that correspond to various eccentricities illumination in determining ocular spherical and cylindrical refractive errors.

12. A method of determining ocular refractive error from a retinal reflex of a photoscreening image comprising:
utilizing information of ocular orientation obtained from a corneal reflection position to determine ocular refractive error.

13. A photoscreening method comprising:
analyzing ocular fixation and motility of a subject;
analyzing abnormalities of each single eye of the subject by analyzing retinal reflex of each eye of the subject in each of the following areas: intensity spatial distribution and gradient of each spectral region of interest; uniformity; and spectral distribution; and comparing signals at regions of interest against predetermined thresholds; and
comparing differences of retinal reflex between two eyes of the subject.

14. A photoscreening method comprising:
analyzing ocular fixation and motility of a subject;
analyzing abnormalities of each single eye of the subject; and
comparing differences of retinal reflex between two eyes of the subject by comparing difference between a left and right eye of the subject in each of the following areas: intensity of spectral region of interest; uniformity; intensity gradient and distribution; and spectrum ratios, regions of interest being compared against predetermined thresholds.

15. A system of automatic computer analysis for photoscreening system that comprises:
an irradiation system that provides multiple angle and axial eccentricity illuminations; and
a computer control system that generates a three-dimensional bell-shape intensity profile based on the multiple angle and axial eccentricity illuminations that is used to detect possible ocular refractive errors and astigmatism of a subject being examined.

16. A photoscreening method comprising:
providing multiple angle and axial eccentricity illuminations used during photoscreening examination of a subject; and
generating a three-dimensional bell-shape intensity profile based on the multiple angle and axial eccentricity illuminations that is used to detect possible ocular refractive errors and astigmatism of the subject being examined.

17. A system of automatic computer analysis for photoscreening system that comprises:
a strabismus module that analyzes ocular fixation and motility;
a single-eye module that analyzes abnormalities of each single eye; and
an eye-correlation module that compares differences of retinal reflex between two eyes, further comprising:
a display for showing a target that moves across the display;
a visual occluder that limits a subject's ability to view the target with both eyes at different points during the target's trajectory across the display; and
a computer control system that detects whether an eye of the subject experiences saccade scattering as the subject is visually tracking the target across the display and determines the subject's Hirschberg ratio and fovea angle based on the subject's gazing trajectory, the gazing trajectory being measured by the computer control system.

18. The system of claim 17, wherein the visual occluder comprises a frame that produces temple side boundaries through which the subject views the target.

19. The system of claim 17, wherein the visual occluder comprises a nasal occluder having a nasal-side boundary about which the subject views the target.

20. The system of claim 17, wherein the visual occluder comprises binocular tubes having a nasal-side boundary about which the subject views the target.

21. A photoscreening method comprising:
analyzing ocular fixation and motility of a subject by determining a subject's convergence and fixation angle and comparing the subject convergence and fixation angle with regions of normal, abnormal, and uncertain results to indicate whether a captured ocular image shows an abnormality related to strabismus;
further comprising:
displaying a target in motion across a display;
limiting a subject's ability to view the target with both eyes at different points during the target's trajectory across the display;
measuring the subject's gazing trajectory as the subject visually tracks movement of the target across the display; and
determining the subject's Hirschberg ratio and fovea angle based on the subject's gazing trajectory.

22. The method of claim 21, further comprising analyzing abnormalities of each single eye of the subject and comparing the differences of retinal reflex between two eyes of the subject.

* * * * *

UNITED STATES PATENT AND TRADEMARK OFFICE
CERTIFICATE OF CORRECTION

| | | |
|---|---|---|
| PATENT NO. | : 7,878,652 B2 | Page 1 of 1 |
| APPLICATION NO. | : 12/234947 | |
| DATED | : February 1, 2011 | |
| INVENTOR(S) | : Ying-Ling Ann Chen and James W. L. Lewis | |

It is certified that error appears in the above-identified patent and that said Letters Patent is hereby corrected as shown below:

Column 1, lines 9-10, delete "herein by reference" and replace with --herein by reference.--

Column 7, line 2, delete "may be use to" and replace with --may be used to--

Column 9, lines 44-48, delete
"There is considerable population distribution scatter of the HR and Kobserved due to influences from subject differences. Therefore, a subject's actual HR and Kvalues may differ significantly from the assumed values of HR and Kbased on population distributions"
and replace with --There is considerable population distribution scatter of the HR and K observed due to influences from subject differences. Therefore, a subject's actual HR and K values may differ significantly from the assumed values of HR and K based on population distributions--

Column 9, lines 49-51, delete
"Accordingly, in one embodiment, inter-subject variance of HR and Kis taken into account by APS 100 to accurately measure the strabismic angle"
and replace with --Accordingly, in one embodiment, inter-subject variance of HR and K is taken into account by APS 100 to accurately measure the strabismic angle--

Column 14, line 46, delete "calibrated and normalize" and replace with --calibrated and normalized--

Column 18, line 21, delete "and detectors 142, 150 that span" and replace with --and detector 150 that span--

Column 18, lines 54-55, delete "(e.g., data (date/year of birth, gender, race, reside area, ID code, etc.)" and replace with --(e.g., data (date/year of birth, gender, race, reside area, ID code, etc.))--

Signed and Sealed this
Twentieth Day of March, 2012

David J. Kappos
*Director of the United States Patent and Trademark Office*